United States Patent
Ito

(10) Patent No.: US 8,541,533 B2
(45) Date of Patent: Sep. 24, 2013

(54) FLUORINE-CONTAINING POLYFUNCTIONAL SILICON COMPOUND AND METHOD FOR PRODUCING FLUORINE-CONTAINING POLYFUNCTIONAL SILICON COMPOUND

(75) Inventor: Takayuki Ito, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 319 days.

(21) Appl. No.: 12/867,301

(22) PCT Filed: Feb. 12, 2009

(86) PCT No.: PCT/JP2009/052323
§ 371 (c)(1),
(2), (4) Date: Aug. 12, 2010

(87) PCT Pub. No.: WO2009/101986
PCT Pub. Date: Aug. 20, 2009

(65) Prior Publication Data
US 2010/0324253 A1  Dec. 23, 2010

(30) Foreign Application Priority Data
Feb. 12, 2008 (JP) ................. 2008-030698

(51) Int. Cl.
*C08G 77/24* (2006.01)
(52) U.S. Cl.
USPC ............................................ 528/29; 528/42
(58) Field of Classification Search
USPC .................................................... 529/29, 42
See application file for complete search history.

(56) References Cited

U.S. PATENT DOCUMENTS

| | | | |
|---|---|---|---|
| 6,613,860 B1 * | 9/2003 | Dams et al. ..................... | 528/36 |
| 7,094,471 B2 * | 8/2006 | Moore et al. .................... | 428/447 |
| 2003/0124361 A1 * | 7/2003 | Moore et al. .................... | 428/447 |
| 2004/0263952 A1 | 12/2004 | Taylor-Smith | |

FOREIGN PATENT DOCUMENTS

| | | |
|---|---|---|
| CN | 1290288 A | 4/2001 |
| EP | 1 055 718 | * 11/2000 |
| EP | 1 055 718 A1 | 11/2000 |
| JP | 09-40680 A | 2/1997 |
| JP | 09-176323 A | 7/1997 |
| JP | 11-002703 A | 1/1999 |
| JP | 11-035585 A | 2/1999 |
| JP | 11-116943 A | 4/1999 |
| JP | 2000-321401 A | 11/2000 |
| JP | 2000-327997 A | 11/2000 |
| JP | 2000-328230 A | 11/2000 |
| JP | 2005-508420 A | 3/2005 |
| JP | 2008-106036 A | 5/2008 |
| JP | 2008-134585 A | 6/2008 |
| JP | 2008-280294 A | 11/2008 |
| WO | 02/30848 A1 | 4/2002 |
| WO | 2005-059051 A1 | 6/2005 |
| WO | 2005-121156 A1 | 12/2005 |
| WO | 2008-087946 A1 | 7/2008 |
| WO | 2009-008380 A1 | 1/2009 |

OTHER PUBLICATIONS

English-language translation of the Written Opinion (PCT/ISA/237) for PCT/2009/052323 dated Apr. 21, 2009.
International Search Report (PCT/ISA/210)for PCT/JP2009/052323, dated Apr. 21, 2009.
Written Opinion (PCT/ISA/237)for PCT/JP2009/052323, dated Apr. 21, 2009.
Yukishige Kondo, et al.; "Synthesis of α, ω-Bissilanes with Fluorocarbon Chain and Surface Structures of Solid Surfaces Modified with Silanes"; J. Oleo Sci; 2005; vol. 51 No. 5; pp. 305-311.
The Chemical Society of Japan, 4th Edition Jikken Kagazu Kozo, 20, Yuki Gosei II—Alcohol Amine—, Maruzen Co., Ltd.; 1992; pp. 355-358.
Office Action dated Feb. 16, 2013in Chinese Application No. 200980104809.6.
Office Action dated Jan. 29, 2013 in Japanese Application No. 2009-553446.
Jikken Kagaku Koza 20, Yuki Gosei II—Alcohol Amine, 1st edition, The Chemical Society of Japan, Maruzen, 1992, pp. 355-358.

* cited by examiner

Primary Examiner — Margaret Moore
(74) Attorney, Agent, or Firm — Sughrue Mion, PLLC

(57) ABSTRACT

A fluorine-containing polyfunctional silicon compound represented by the following general formula (I), which is useful as a raw material for materials having high water repellency and excellent scratch resistance and water droplet sliding properties and which can be produced by a production method which is simple and easy and environmentally friendly, is provided.

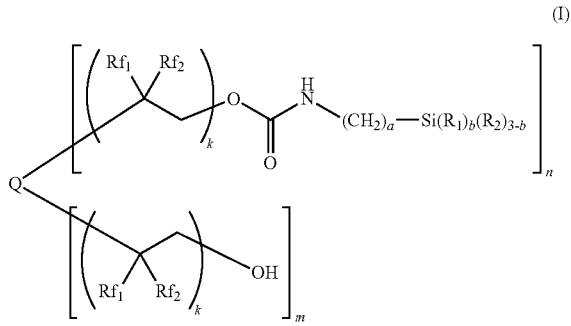

(I)

In the formula, Q represents an (n+m)-valent organic group having at least one fluorine atom; each of $Rf_1$ and $Rf_2$ independently represents a fluorine atom, a hydrogen atom or an alkyl group having at least one fluorine atom; $R_1$ represents a hydroxyl group, an isocyanate group or a hydrolyzable group; $R_2$ represents a hydrogen atom or a hydrocarbon group; k represents 0 or 1; n represents an integer of 2 or more; m represents an integer of 0 or more; a represents an integer of from 1 to 6; and b represents an integer of from 1 to 3.

14 Claims, No Drawings

FLUORINE-CONTAINING POLYFUNCTIONAL SILICON COMPOUND AND METHOD FOR PRODUCING FLUORINE-CONTAINING POLYFUNCTIONAL SILICON COMPOUND

TECHNICAL FIELD

The present invention relates to a novel fluorine-containing polyfunctional silicon compound capable of serving as a raw material for materials having characteristics such as weather resistance, heat resistance, chemical resistance, low refraction properties, water and oil repellency, water droplet sliding properties, lubricity, release properties, etc. and to a method for producing the same.

BACKGROUND ART

Fluorine atom-containing polycondensable silicon compounds are useful as a raw material for materials having characteristics such as weather resistance, heat resistance, chemical resistance, low refraction properties, water and oil repellency, water droplet sliding properties, lubricity, release properties, etc., and for example, compounds represented by $CF_3(CF_2)_nCH_2CH_2SiX_3$ (wherein n represents an integer of from about 3 to 10; and X represents a chlorine atom, an alkoxy group, an isocyanate group, etc.) are known. Though polymer materials, film materials, coating agents and the like obtained from these raw materials exhibit high water repellency, they were not satisfactory from the viewpoints of strength and scratching properties because only one condensable silicon group is present in one molecule. Also, there was involved a problem in water droplet sliding properties.

From the viewpoint of enhancing the scratch resistance, there is known an example utilizing a fluorine-containing compound having two trialkoxysilyl groups in one molecule, represented by $(RO)_3SiCH_2CH_2(CF_2)_nCH_2CH_2Si(OR)_3$ (see Patent Document 1). However, though such a compound is, for example, obtained by allowing a fluorine-containing diene compound represented by $CH_2=CH(CF_2)_nCH=CH_2$, trichlorosilane and a Pt catalyst to react in a sealed tube at 100° C. for 50 hours, followed by treating with sodium methoxide (see Non-Patent Document 1), it is difficult to economically produce the compound on an industrial scale. Also, the raw material fluorine-containing diene is problematic in production aptitude and availability.

Also, from the viewpoint of enhancing the water droplet sliding properties, there is known an example utilizing a compound such as $CH_3(CF_2)_nCH_2CH_2Si(OR)$, etc. (see Patent Document 2). However, with respect to such a compound, a reaction between a fluorine-containing olefin compound represented by $CH_3(CF_2)_nCH=CH_2$ and trichlorosilane is necessary, and there were involved problems in production aptitude and availability of the fluorine-containing olefin.

As a method for simply and easily producing a fluorine atom-containing polycondensable silicon compound, there is known an example in which a fluorine-containing alcohol, $CF_3(CF_2)_nCH_2OH$ and an isocyanate group-containing polycondensable silicon compound are allowed to react in the presence of an Sn catalyst to obtain a carbamic acid ester in a high yield (see Patent Document 3). However, an example for applying to a polyfunctional alcohol has not been known yet. Also, the Sn catalyst is not preferable from the environmental standpoint.

Patent Document 1: WO 05/059051
Patent Document 2: JP-A-11-116943
Patent Document 3: WO 05/121156
Non-Patent Document 1: *Journal of Oleo Science*, 51(5), pages 305 to 311 (2002)

DISCLOSURE OF THE INVENTION

Problems that the Invention is to Solve

The invention is aimed to provide a fluorine-containing polyfunctional silicon compound which is useful as a raw material for materials having high water repellency and excellent scratch resistance and water droplet sliding properties and which can be produced by a production method which is simple, easy, and environmentally friendly. Also, the invention is aimed to provide a method for producing the fluorine-containing polyfunctional silicon compound, which is simple and easy and environmentally friendly.

Means for Solving the Problems

In order to attain the foregoing objects, the present inventor made extensive and intensive investigations. As a result, the present inventor has accomplished the invention according to the following means. That is, according to this application, the following inventions are provided.

1. A fluorine-containing polyfunctional silicon compound represented by the following general formula (I):

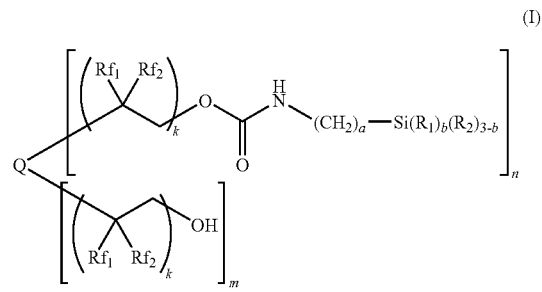

(In the formula, Q represents an (n+m)-valent organic group having at least one fluorine atom; each of $Rf_1$ and $Rf_2$ independently represents a fluorine atom, a hydrogen atom or an alkyl group having at least one fluorine atom; $R_1$ represents a hydroxyl group, an isocyanate group or a hydrolyzable group; $R_2$ represents a hydrogen atom or a hydrocarbon group; k represents 0 or 1; n represents an integer of 2 or more; m represents an integer of 0 or more; a represents an integer of from 1 to 6; and b represents an integer of from 1 to 3.)

2. The fluorine-containing polyfunctional silicon compound as set forth above in 1, which is characterized in that in the general formula (I), Q represents a perfluoroalkyl group; each of $Rf_1$ and $Rf_2$ independently represents a fluorine atom or a perfluoroalkyl group; and k represents 1.

3. The fluorine-containing polyfunctional silicon compound as set forth above in 1, which is characterized in that the fluorine-containing polyfunctional silicon compound represented by the general formula (I) is a compound represented by the following general formula (II):

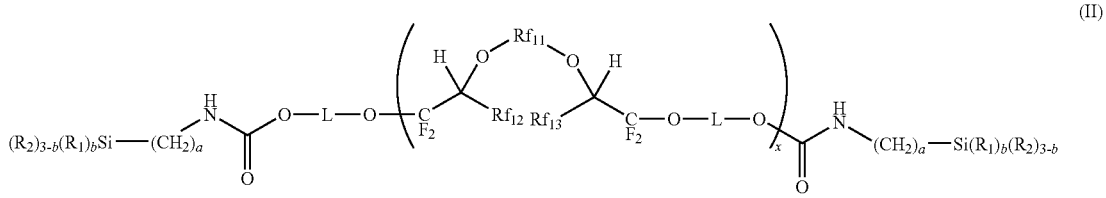

(In the formula, $R_1$ represents a hydroxyl group, an isocyanate group or a hydrolyzable group; $R_2$ represents a hydrogen atom or a hydrocarbon group; a represents an integer of from 1 to 6; b represents an integer of from 1 to 3; x represents an integer of from 1 to 200; L represents a divalent organic group; $Rf_{11}$ represents a perfluoroalkylene group; each of $Rf_{12}$ and $Rf_{13}$ independently represents a fluorine atom, a perfluoroalkyl group or a perfluoroalkoxy group; and at least two of $Rf_{11}$, $Rf_{12}$ and $Rf_{13}$ may be bonded to each other to form one or more rings.)

4. The fluorine-containing polyfunctional silicon compound as set forth above in 3, which is characterized in that the fluorine-containing polyfunctional silicon compound represented by the general formula (II) is a compound represented by the following general formula (III):

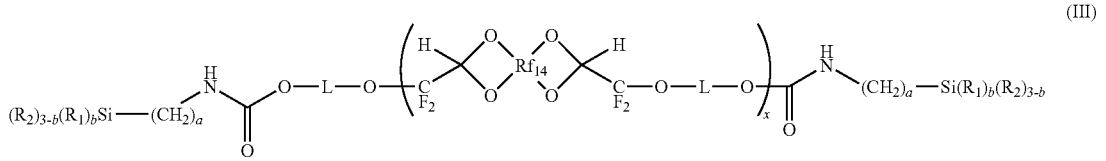

(In the formula, $R_1$ represents a hydroxyl group, an isocyanate group or a hydrolyzable group; $R_2$ represents a hydrogen atom or a hydrocarbon group; a represents an integer of from 1 to 6; b represents an integer of from 1 to 3; x represents an integer of from 1 to 200; L represents a divalent organic group; and $Rf_{14}$ represents a tetravalent perfluoroalkylene group.)

5. The fluorine-containing polyfunctional silicon compound as set forth above in 4, which is characterized in that the fluorine-containing polyfunctional silicon compound represented by the general formula (III) is a compound represented by the following general formula (IV):

(In the formula, $R_1$ represents a hydroxyl group, an isocyanate group or a hydrolyzable group; $R_2$ represents a hydrogen atom or a hydrocarbon group; a represents an integer of from 1 to 6; b represents an integer of from 1 to 3; x represents an integer of from 1 to 200; and L represents a divalent organic group.)

6. The fluorine-containing polyfunctional silicon compound as set forth above in any one of 3 to 5, which is characterized in that L is a divalent organic group represented by the following general formula (V) or (VI):

$$-CH_2-Rf_{15}-CH_2- \quad (V)$$

$$-Ar_1- \quad (VI)$$

(In the formulae, $Rf_{15}$ represents a divalent perfluoroalkyl group; and $Ar_1$ represents a divalent aryl group.)

7. A method for producing a fluorine-containing polyfunctional silicon compound represented by the following general formula (I), which is characterized by allowing an (n+m)-valent fluorine-containing alcohol represented by the following general formula (I) and an isocyanate represented by the general formula (VII) to react under a basic condition:

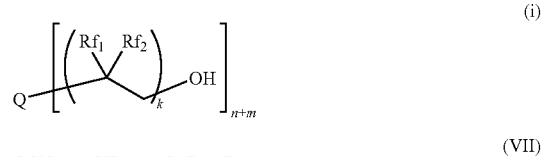

$$OCN-(CH_2)_a-Si(R_1)_b(R_2)_{3-b} \quad (VII)$$

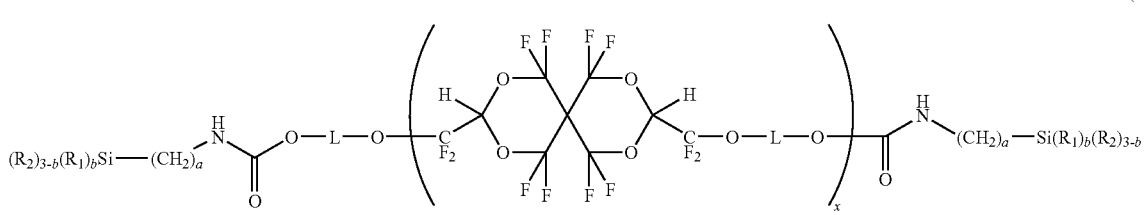

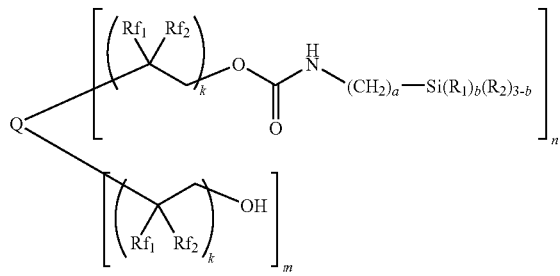

(I)

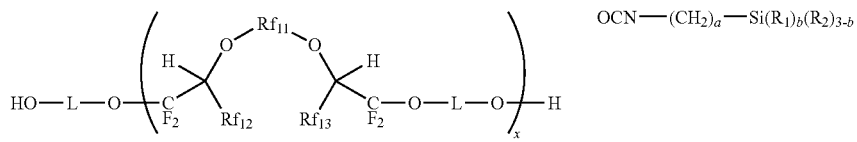

(ii)

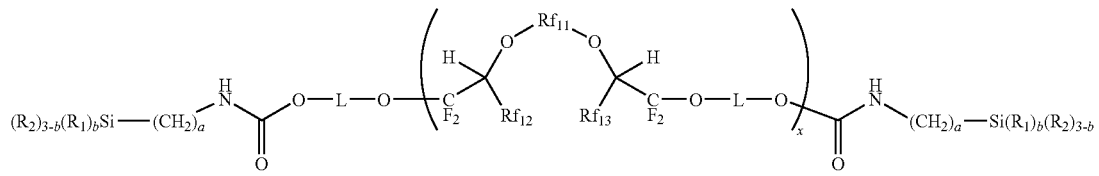

(II)

(In the formulae, Q represents an (n+m)-valent organic group having at least one fluorine atom; k represents 0 or 1; each of $Rf_1$ and $Rf_2$ independently represents a fluorine atom, a hydrogen atom or an alkyl group having at least one fluorine atom; $R_1$ represents a hydroxyl group, an isocyanate group or a hydrolyzable group; $R_2$ represents a hydrogen atom or a hydrocarbon group; n represents an integer of 2 or more; m represents an integer of 0 or more; a represents an integer of from 1 to 6; and b represents an integer of from 1 to 3.)

8. A method for producing of a fluorine-containing polyfunctional silicon compound represented by the following general formula (II), which is characterized by allowing a fluorine-containing alcohol represented by the following general formula (ii) and an isocyanate represented by the following general formula (VII) to react under a basic condition:

$$OCN-(CH_2)_a-Si(R_1)_b(R_2)_{3-b}$$ (VII)

(In the formulae, $R_1$ represents a hydroxyl group, an isocyanate group or a hydrolyzable group; $R_2$ represents a hydrogen atom or a hydrocarbon group; a represents an integer of from 1 to 6; b represents an integer of from 1 to 3; x represents an integer of from 1 to 200; L represents a divalent organic group; $Rf_{11}$ represents a perfluoroalkylene group; each of $Rf_{12}$ and $Rf_{13}$ independently represents a fluorine atom, a perfluoroalkyl group or a perfluoroalkoxy group; and at least two of $Rf_{11}$, $Rf_{12}$ and $Rf_{13}$ may be bonded to each other to form one or more rings.)

9. A method for producing of a fluorine-containing polyfunctional silicon compound represented by the following general formula (III), which is characterized by allowing a fluorine-containing alcohol represented by the following general formula (iii) and an isocyanate represented by the following general formula (VII) to react under a basic condition:

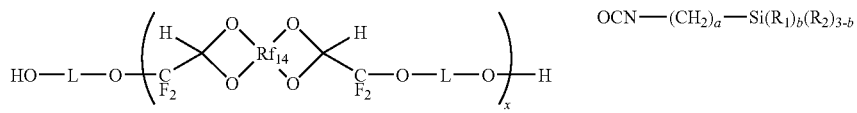

(iii)

$$OCN-(CH_2)_a-Si(R_1)_b(R_2)_{3-b}$$ (VII)

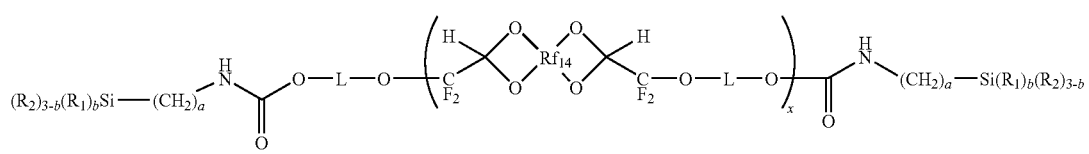

(III)

(In the formulae, $R_1$ represents a hydroxyl group, an isocyanate group or a hydrolyzable group; $R_2$ represents a hydrogen atom or a hydrocarbon group; a represents an integer of from 1 to 6; b represents an integer of from 1 to 3; x represents an integer of from 1 to 200; L represents a divalent organic group; and $Rf_{14}$ represents a tetravalent perfluoroalkylene group.)

10. A method for producing of a fluorine-containing polyfunctional silicon compound represented by the following general formula (IV), which is characterized by allowing a fluorine-containing alcohol represented by the following general formula (iv) and an isocyanate represented by the following general formula (VII) to react under a basic condition:

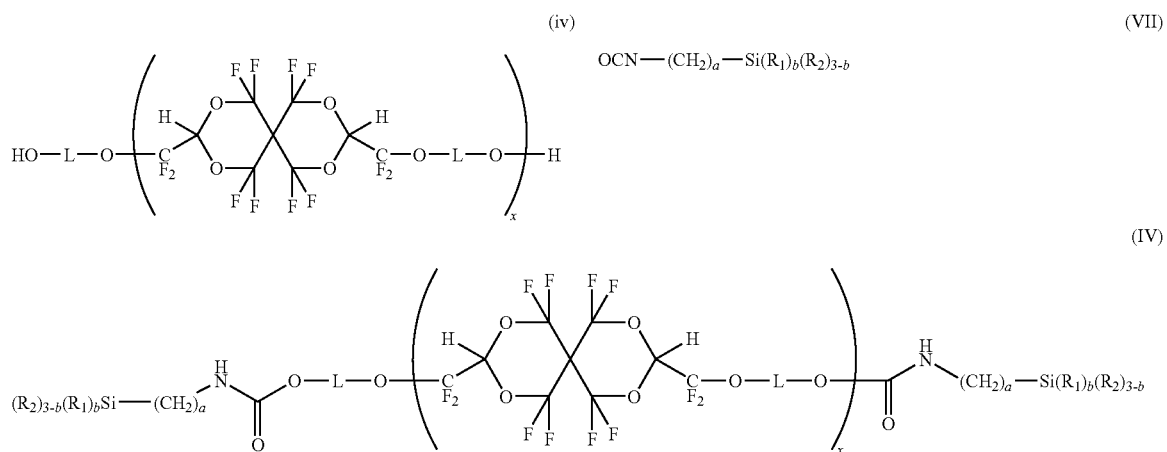

(In the formulae, $R_1$ represents a hydroxyl group, an isocyanate group or a hydrolyzable group; $R_2$ represents a hydrogen atom or a hydrocarbon group; a represents an integer of from 1 to 6; b represents an integer of from 1 to 3; x represents an integer of from 1 to 200; and L represents a divalent organic group.)

11. The method for producing of a fluorine-containing polyfunctional silicon compound as set forth above in any one of 8 to 10, which is characterized in that L is a divalent organic group represented by the following general formula (V) or (VI):

$$—CH_2—Rf_{15}—CH_2— \quad (V)$$

(In the formulae, $Rf_{15}$ represents a divalent perfluoroalkyl group; and $Ar_1$ represents a divalent aryl group.)

12. A processed substrate, which is characterized by comprising a substrate having thereon a film formed of a composition containing the fluorine-containing polyfunctional silicon compound as set forth above in any one of 1 to 6.

Advantages of the Invention

According to the invention, a fluorine-containing polyfunctional silicon compound capable of serving as a raw material for polymer materials, film materials, coating agents and the like which are excellent from the viewpoints of water repellency and water droplet sliding properties can be produced by a method which is simple, easy, and environmentally friendly. Also, by using such a fluorine-containing polyfunctional silicon compound as a raw material, a water-repellent material which is excellent in scratch resistance and water droplet sliding properties can be obtained as compared with the case of using a conventional fluorine-containing silicon compound as a raw material.

BEST MODES FOR CARRYING OUT THE INVENTION

The fluorine-containing polyfunctional silicon compound of the invention is represented by the following general formula (I).

In the general formula (I), Q represents an (n+m)-valent organic group having at least one fluorine atom; each of $Rf_1$ and $Rf_2$ independently represents a fluorine atom, a hydrogen atom or an alkyl group having at least one fluorine atom; $R_1$ represents a hydroxyl group, an isocyanate group or a hydrolyzable group; $R_2$ represents a hydrogen atom or a hydrocarbon group; k represents 0 or 1; n represents an integer of 2 or more; m represents an integer of 0 or more; a represents an integer of from 1 to 6; and b represents an integer of from 1 to 3.

In the case where plural $R_1$s or $R_2$s are present, each $R_1$ or $R_2$ may be the same as or different from every other $R_1$ or $R_2$.

In the general formula (I), $R_1$ represents a hydroxyl group, an isocyanate group or a hydrolyzable group. Here, the hydrolyzable group refers to a group capable of being converted into a hydroxyl group upon a hydrolysis reaction, and examples thereof include a halogen atom (for example, a fluorine atom, a chlorine atom, a bromine atom, an iodine atom, etc.), an alkoxy group (for example, a methoxy group, an ethoxy group, a propoxy group, a butoxy group, etc.), an acyloxy group (for example, an acetyloxy group, a propionyloxy group, etc.) and the like. $R_1$ is preferably a hydroxyl group or an alkoxy group, and especially preferably a hydroxyl group, a methoxy group or an ethoxy group.

$R_2$ represents a hydrogen atom or a hydrocarbon group. The hydrocarbon group represented by $R_2$ is preferably a substituted or unsubstituted, linear, branched or cyclic alkyl group having from 1 to 20 carbon atoms (more preferably from 1 to 10 carbon atoms), a substituted or unsubstituted, linear, branched or cyclic alkenyl group having from 1 to 20 carbon atoms (more preferably from 1 to 10 carbon atoms), a substituted or unsubstituted, linear, branched or cyclic alkynyl group having from 1 to 20 carbon atoms (more preferably from 1 to 10 carbon atoms) or a substituted or unsubstituted aryl group having from 6 to 20 carbon atoms (more preferably from 6 to 10 carbon atoms); and more preferably a methyl group, an ethyl group, a vinyl group, an allyl group or a phenyl group.

$R_2$ is preferably a hydrogen atom, a methyl group, an ethyl group or a phenyl group, and more preferably a methyl group or an ethyl group.

Examples of the substituent include the following substituents. There are exemplified a halogen atom (for example, a fluorine atom, a chlorine atom, a bromine atom and an iodine atom), an alkyl group having not more than 18 carbon atoms (for example, methyl and ethyl), an aryl group having not more than 18 carbon atoms (for example, phenyl and naphthyl), a cyano group, a carboxyl group, an alkoxycarbonyl group having not more than 18 carbon atoms (for example, methoxycarbonyl), an aryloxycarbonyl group having not more than 18 carbon atoms (for example, phenoxycarbonyl), a carbamoyl group (for example, carbamoyl, N-phenylcarbamoyl and N, N-dimethylcarbamoyl), an alkylcarbonyl group having not more than 18 carbon atoms (for example, acetyl), an arylcarbonyl group having not more than 18 carbon atoms (for example, benzoyl), a nitro group, an amino group (for example, amino, dimethylamino and anilino), an acylamino group having not more than 18 carbon atoms (for example, acetamide and ethoxycarbonylamino), a sulfonamide group (for example, methanesulfonamide), an imide group (for example, succinimide and phthalimide), an imino group (for example, benzylideneamino), a hydroxyl group, an alkoxy group having not more than 18 carbon atoms (for example, methoxy), an aryloxy group having not more than 18 carbon atoms (for example, phenoxy), an acyloxy group having not more than 18 carbon atoms (for example, acetoxy), an alkylsulfonyloxy group having not more than 18 carbon atoms (for example, methanesulfonyloxy), an arylsulfonyloxy group having not more than 18 carbon atoms (for example, benzenesulfonyloxy), a sulfo group, a sulfamoyl group (for example, sulfamoyl and N-phenylsulfamoyl), an alkylthio group having not more than 18 carbon atoms (for example, methylthio), an arylthio group having not more than 18 carbon atoms (for example, phenylthio), an alkylsulfonyl group having not more than 18 carbon atoms (for example, methanesulfonyl), an arylsulfonyl group having not more than 18 carbon atoms (for example, benzenesulfonyl), a heterocyclic group and the like. Such a substituent may be further substituted, and in the case where plural substituents are present, each substituent may be the same as or different from every other substituent. Also, the substituents may be bonded to each other to form a ring.

a represents an integer of from 1 to 6, and preferably 3. b represents an integer of from 1 to 3, and preferably 3.

In the general formula (I), Q represents an (n+m)-valent organic group having at least one fluorine atom.

Each of $Rf_1$ and $Rf_2$ independently represents a fluorine atom, a hydrogen atom or an alkyl group having at least one fluorine atom. The alkyl group having at least one fluorine atom may have a substituent or may be unsubstituted and may be linear, branched or cyclic. Also, the alkyl group may have an ethereal oxygen atom in the chain and preferably has from 1 to 10 carbon atoms. Each of $Rf_1$ and $Rf_2$ is preferably a fluorine atom or a perfluoroalkyl group (for example, perfluoromethyl, perfluoroethyl, perfluoropropyl and perfluoroisopropyl), and more preferably a fluorine atom.

k represents 0 or 1, and k preferably represents 1. n represents an integer of 2 or more; m represents an integer of 0 or more; preferably, (n+m) represents an integer of 2 or more and not more than 10, and m represents an integer of not more than 5; and more preferably, (n+m) represents an integer of 3 or more and not more than 6, and m represents an integer of not more than 3.

Q is preferably a linear, branched or cyclic, (n+m)-valent perfluoroalkyl group having from 1 to 30 (more preferably from 1 to 20, and further preferably from 1 to 10) carbon atoms, which may have an ethereal oxygen atom, or a divalent organic group for constituting a compound represented by the following general formula (II).

In the fluorine-containing polyfunctional silicon compound represented by the foregoing general formula (I), the case where Q represents a perfluoroalkyl group, each of $Rf_1$ and $Rf_2$ independently represents a fluorine atom or a perfluoroalkyl group, and k represents 1 is preferable.

Also, the fluorine-containing polyfunctional silicon compound represented by the foregoing general formula (I) is preferably a compound represented by the following general formula (II).

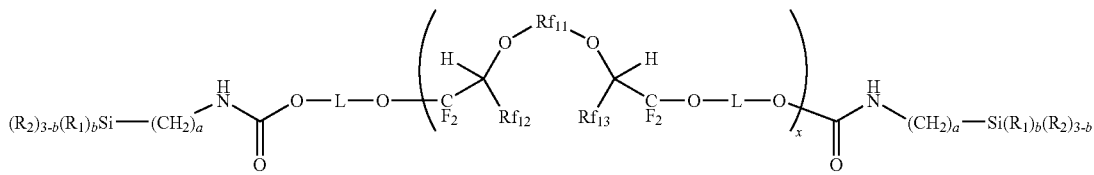

(II)

In the general formula (II), $R_1$ represents a hydroxyl group, an isocyanate group or a hydrolyzable group; $R_2$ represents a hydrogen atom or a hydrocarbon group; a represents an integer of from 1 to 6; b represents an integer of from 1 to 3; x represents an integer of from 1 to 200; L represents a divalent organic group; $Rf_{11}$ represents a perfluoroalkylene group; each of $Rf_{12}$ and $Rf_{13}$ independently represents a fluorine atom, a perfluoroalkyl group or a perfluoroalkoxy group; and at least two of $Rf_{11}$, $Rf_{12}$ and $Rf_{13}$ may be bonded to each other to form one or more rings.

In the case where plural $R_1$s, $R_2$s, $Rf_{11}$s, $Rf_{12}$s, $Rf_{13}$s or Ls are present, each $R_1$, $R_2$, $Rf_{11}$, $Rf_{12}$, $Rf_{13}$ or L may be the same as or different from every other $R_1$, $R_2$, $Rf_{11}$, $Rf_{12}$, $Rf_{13}$ or L.

The perfluoroalkylene group represented by $Rf_{11}$ is preferably a perfluoroalkylene group having from 1 to 30 carbon atoms and may be linear, branched or cyclic, and it may have an ether bond in the chain. The perfluoroalkylene group represented by $Rf_{11}$ has more preferably from 1 to 20 carbon atoms, and further preferably from 2 to 10 carbon atoms.

The perfluoroalkyl group represented by each of $Rf_{12}$ and $Rf_{13}$ is preferably a perfluoroalkyl group having from 1 to 30 carbon atoms and may be linear, branched or cyclic, and it may have an ether bond in the chain. The perfluoroalkyl group represented by each of $Rf_{12}$ and $Rf_{13}$ has more preferably from 1 to 20 carbon atoms, and further preferably from 1 to 10 carbon atoms.

The perfluoroalkoxy group represented by each of $Rf_{12}$ and $Rf_{13}$ is preferably a perfluoroalkoxy group having from 1 to 30 carbon atoms and may be linear, branched or cyclic, and it may have an ether bond in the chain. The perfluoroalkoxy group represented by each of $Rf_{12}$ and $Rf_{13}$ has more preferably from 1 to 20 carbon atoms, and further preferably from 1 to 10 carbon atoms.

In the general formula (II), preferred examples of $R_1$, $R_2$, a and b are the same as those of $R_1$, $R_2$, a and b in the foregoing general formula (I).

In the general formula (II), it is preferable that $Rf_{12}$ or $Rf_{13}$, and preferably both of $Rf_{12}$ and $Rf_{13}$ are a fluorine atom or a perfluoroalkoxy group; and in the case where both of $Rf_{12}$ and $Rf_{13}$ are a perfluoroalkoxy group, the compound represented by the general formula (II) is more preferably a compound represented by the following general formula (III).

The tetravalent perfluoroalkylene group represented by $Rf_{14}$ is preferably a perfluoroalkylene group having from 1 to 30 carbon atoms and may be linear, branched or cyclic, and it may have an ether bond in the chain. The tetravalent perfluoroalkylene group represented by $Rf_{14}$ has more preferably from 4 to 20 carbon atoms, and further preferably from 5 to 10 carbon atoms.

In the general formula (III), preferred examples of $R_1$, $R_2$, a and b are the same as those of $R_1$, $R_2$, a and b in the foregoing general formula (I).

The compound represented by the general formula (III) is preferably a compound represented by the following general formula (IV).

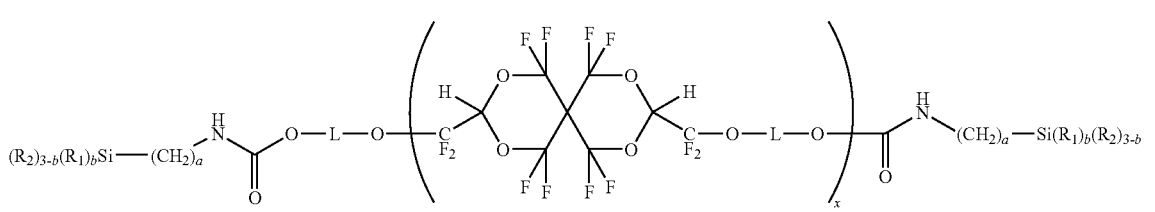

(IV)

In the general formula (IV), $R_1$ represents a hydroxyl group, an isocyanate group or a hydrolyzable group; $R_2$ represents a hydrogen atom or a hydrocarbon group; a represents an integer of from 1 to 6; b represents an integer of from 1 to 3; x represents an integer of from 1 to 200; and L represents a divalent organic group.

In the general formula (IV), preferred examples of $R_1$, $R_2$, a and b are the same as those of $R_1$, $R_2$, a and b in the foregoing general formula (I).

In the general formulae (II) to (IV), x represents an integer of from 1 to 200, preferably from 1 to 50, and more preferably from 1 to 20. The divalent organic group represented by L is preferably a linear, branched or cyclic, divalent organic group having from 1 to 50 carbon atoms, which may have a substituent, and more preferably a divalent organic group represented by the following general formula (V) or the following general formula (VI). Examples of the substituent which the divalent organic group may have include the same groups as those in the substituent for $R_2$.

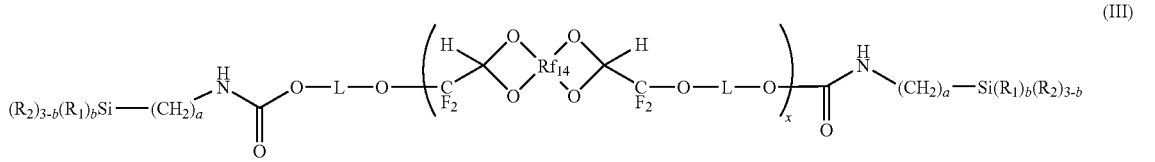

(III)

In the general formula (III), $R_1$ represents a hydroxyl group, an isocyanate group or a hydrolyzable group; $R_2$ represents a hydrogen atom or a hydrocarbon group; a represents an integer of from 1 to 6; b represents an integer of from 1 to 3; x represents an integer of from 1 to 200; L represents a divalent organic group; and $Rf_{14}$ represents a tetravalent perfluoroalkylene group.

In the case where plural $R_1$s, $R_2$s, $Rf_{14}$s or Ls are present, each $R_1$, $R_2$, $Rf_{14}$ or L may be the same as or different from every other $R_1$, $R_2$, $Rf_{14}$ or L.

$$-CH_2-Rf_{15}-CH_2- \quad (V)$$

$$-Ar_1- \quad (VI)$$

In the general formula (V) and general formula (VI), $Rf_{15}$ represents a divalent perfluoroalkyl group; and $Ar_1$ represents a divalent aryl group.

The divalent perfluoroalkyl group represented by $Rf_{15}$ is preferably a perfluoroalkylene group having from 1 to 30 carbon atoms and may be linear, branched or cyclic, and it may have an ether bond in the chain. The divalent perfluoroalkyl group represented by $Rf_{15}$ has preferably from 1 to 20 carbon atoms, and more preferably from 2 to 10 carbon atoms.

The divalent aryl group represented by $Ar_1$ is preferably a substituted or unsubstituted aryl group having from 6 to 30 carbon atoms. The carbon atom number is more preferably from 6 to 20, and further preferably from 6 to 10. Examples of the substituent include the same groups as those in the substituent for $R_2$.

Each of the compounds represented by the general formulae (I) to (IV) can be easily obtained by allowing a fluorine-containing alcohol represented by any one of the following general formulae (i) to (iv) and an isocyanate represented by the following general formula (VII) to react under a basic condition.

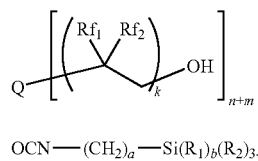

(i)

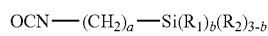

(VII)

In the general formula (I) and general formula (VII), Q represents an (n+m)-valent organic group having at least one fluorine atom; k represents 0 or 1; each of $Rf_1$ and $Rf_2$ independently represents a fluorine atom, a hydrogen atom or an alkyl group having at least one fluorine atom; $R_1$ represents a hydroxyl group, an isocyanate group or a hydrolyzable group; $R_2$ represents a hydrogen atom or a hydrocarbon group; n represents an integer of 2 or more; m represents an integer of 0 or more; a represents an integer of from 1 to 6; and b represents an integer of from 1 to 3.

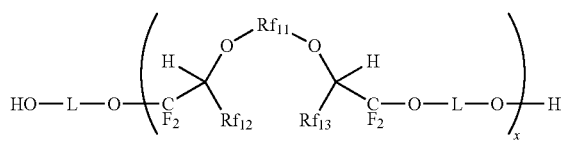

(ii)

In the general formula (II), x represents an integer of from 1 to 200; L represents a divalent organic group; $Rf_{11}$ represents a perfluoroalkylene group; each of $Rf_{12}$ and $Rf_{13}$ independently represents a fluorine atom, a perfluoroalkyl group or a perfluoroalkoxy group; and at least two of $Rf_{11}$, $Rf_{12}$ and $Rf_{13}$ may be bonded to each other to form a ring.

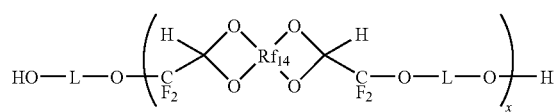

(iii)

In the general formula (iii), x represents an integer of from 1 to 200; L represents a divalent organic group; and $Rf_{14}$ represents a tetravalent perfluoroalkylene group.

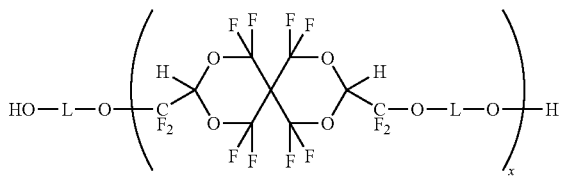

(iv)

In the general formula (Iv), x represents an integer of from 1 to 200; and L represents a divalent organic group.

Specific examples and preferred ranges of respective symbols in the foregoing general formulae (i) to (iv) and general formula (VII) are respectively the same as the definitions, specific examples and preferred ranges of the respective symbols in the foregoing general formulae (I) to (IV).

In the foregoing general formulae (II) to (iv), L is preferably the divalent organic group represented by the foregoing general formula (V) or (VI).

Examples of a base which is used for rendering the system under a basic condition during the reaction between the fluorine-containing alcohol represented by any one of the general formulae (i) to (iv) and the isocyanate represented by the general formula (VII) include inorganic bases such as an alkali metal hydroxide (for example, lithium hydroxide, sodium hydroxide, potassium hydroxide and cesium hydroxide), an alkaline earth metal hydroxide (for example, magnesium hydroxide, calcium hydroxide, strontium hydroxide and barium hydroxide), an alkali metal carbonate (for example, lithium carbonate, sodium carbonate, potassium carbonate and cesium carbonate), an alkaline earth metal carbonate (for example, magnesium carbonate, calcium carbonate, strontium carbonate and barium carbonate), an alkali metal hydrogencarbonate (for example, lithium hydrogencarbonate, sodium hydrogencarbonate, potassium hydrogencarbonate and cesium hydrogencarbonate), an alkaline earth metal hydrogencarbonate (for example, magnesium hydrogencarbonate, calcium hydrogencarbonate, strontium hydrogencarbonate and barium hydrogencarbonate), etc.; and organic bases such as pyridine, picoline, lutidine, collidine, triethylamine, diisopropylethylamine, 1,8-diazabicyclo[5.4.0]undecene, 1,4-diazabicyclo[2.2.2]octane, etc. More preferred examples of the base include sodium carbonate, potassium carbonate, cesium carbonate, triethylamine, diisopropylethylamine, 1,8-diazabicyclo[5.4.0]undecene, 1,4-diazabicyclo[2.2.2]octane and the like, with potassium carbonate and cesium carbonate being especially preferable. A molar equivalent number of the used base is preferably from 0.1 equivalents to 10 equivalents, and more preferably from 0.5 equivalents to 5 equivalents to the hydroxyl group in the compound represented by the general formula (i), (ii), (iii) or (iv).

The reaction between the fluorine-containing alcohol and the isocyanate represented by the general formula (VII) may be carried out using a catalyst or may be carried out without using a catalyst. In general, since this reaction proceeds under a condition suited for the production even in the absence of a catalyst, it is preferable that the reaction is carried out without using a catalyst. In the case of using a catalyst, preferred examples of the catalyst include an ammonium salt (for example, tetrabutylammonium hydroxide, tetrabutylammonium chloride, 1-ethylpyridinium chloride, 1,3-dimethylimidazolium tetrafluoroborate, etc.), a phosphonium salt (for example, triphenyl phosphonium chloride, etc.), a sulfonium salt (for example, triphenyl sulfonium hexafluorophosphate, etc.) and a transition metal catalyst (for example, an iron chloride-acetylacetone complex, etc.).

It is preferable that the reaction between the fluorine-containing alcohol represented by any one of the general formulae (i) to (iv) and the isocyanate represented by the general formula (VII) is carried out in a solvent. Preferred examples of the solvent include a general solvent such as dichloromethane, chloroform, carbon tetrachloride, diethyl ether, dibutyl ether, cyclopentylmethyl ether, diglyme, tetrahydrofuran, dioxane, acetone, ethyl acetate, butyl acetate, acetone, methyl ethyl ketone, cyclohexanone, hexane, heptane, toluene, xylene, acetonitrile, N,N-dimethylformamide, N,N-dimethylacetamide, 1-methylpyrrolidone, 1,3-dimethyl-2-imidazolidinone, dimethyl sulfoxide, etc.;

a fluorine-containing solvent such as AK-225 (a registered trademark, manufactured by Asahi Glass Co., Ltd.), 2,2,2-trifluoroethyl methyl ether, 2,2,2-trifluoroethyl difluoromethyl ether, 2,2,3,3,3-pentafluoropropyl methyl ether, 2,2,3,3,3-pentafluoropropyl difluoromethyl ether, 2,2,3,3,3-pentafluoropropyl-1,1,2,2-tetrafluoroethylether, 1,1,2,2-tetrafluoroethyl methyl ether, 1,1,2,2-tetrafluoroethyl ethyl ether, 1,1,2,2-tetrafluoroethyl-2,2,2-trifluoroethyl ether, 2,2,3,3-tetrafluoropropyl difluoromethyl ether, 1,1,2,2-tetrafluoroethyl-2,2,3,3-tetrafluoropropyl ether, hexafluoroisopropyl methyl ether, 1,1,3,3,3-pentafluoro-2-trifluomethylpropyl methyl ether, 1,1,2,3,3,3-hexafluoropropyl methyl ether, 1,1,2,3,3,3-hexafluoropropyl ethyl ether, 2,2,3,4,4,4-hexafluorobutyl difluoromethyl ether, fluorobenzene, 1,2-difluorobenzene, 1,3-difluorobenzene, 1,4-difluorobenzene, 2,4-difluorotoluene, 2,6-difluorotoluene, 3,4-difluorotoluene, 1,2,3-trifluorobenzene, 1,2,4-trifluorobenzene, 1,3,5-trifluorobenzene, 2,3,4-trifluorotoluene, 1,2,3,4-tetrafluorobenzene, 1,2,3,5-tetrafluorobenzene, 1,2,4,5-tetrafluorobenzene, pentafluorobenzene, hexafluorobenzene, $\alpha,\alpha,\alpha$-trifluoromethylbenzene, 1,3-bis(trifluoromethyl)benzene, 1,4-bis(trifluoromethyl)benzene, etc.;

a perfluoro solvent such as a perfluoroalkane compound [for example, FC-72 (a trade name, manufactured by Sumitomo 3M Limited), etc.], a perfluoro ether compound [for example, FC-75 and FC-77 (both of which are a trade name, manufactured by Sumitomo 3M Limited), etc.], a perfluoro polyether compound [for example, trade names: KRYTOX (a registered trademark), manufactured by DuPont, FOMBLIN (a registered trademark), manufactured by AUSIMONT, GALDEN (a registered trademark), manufactured by AUSIMONT, DEMNUM (manufactured by Daikin Industries Ltd.), etc.], a chlorofluorocarbon compound (for example, CFC-11, CFC-113, etc.), a chlorofluoro polyether compound, a perfluoro trialkylamine compound, an inert fluid (for example, a trade name: FLUORINERT (a registered trademark), manufactured by Sumitomo 3M Limited, etc.) and the like; water; and a mixed solvent thereof.

More preferred examples of the solvent include diethyl ether, dibutyl ether, cyclopentyl methyl ether, diglyme, tetrahydrofuran, dioxane, ethyl acetate, butyl acetate, acetone, methyl ethyl ketone, cyclohexanone, acetonitrile, AK-225 (a registered trademark), manufactured by Asahi Glass Co., Ltd.) and a fluorine-containing ether based solvent such as 2,2,2-trifluoroethyl methyl ether, 2,2,2-trifluoroethyl difluoromethyl ether, etc.

The solvent is used in an amount of preferably from 0.1 times to 100 times, more preferably 1 time to 50 times, and further preferably from 2 times to 20 times relative to the compound represented by the general formula (i), (ii), (iii) or (iv) in terms of a mass ratio.

The isocyanate represented by the general formula (VII) is used in an amount of preferably from 0.5 molar equivalents to 2.0 molar equivalents, and more preferably from 0.9 molar equivalents to 1.1 molar equivalents relative to the hydroxyl group in the compound represented by the general formula (i), (ii), (iii) or (iv).

A reaction temperature is preferably from 0° C. to 100° C., and more preferably from 10° C. to 50° C.

Though a reaction time cannot be unequivocally determined because it varies depending upon the kind, amount and reaction temperature of each of the used substrate, base and solvent, etc., it is preferably from 10 minutes to 12 hours, and more preferably from 30 minutes to 6 hours.

As a post-treatment and a purification method, purification may be carried out by after a usual liquid separation operation, performing concentration and subjecting a residue to distillation, column chromatography or recrystallization. However, the desired material may also be obtained by using a solid base such as potassium carbonate, cesium carbonate, etc. and after the reaction, removing such a solid base by means of filtration, followed by performing only a concentration operation. Also, a filtrate can be used as a solution of the desired material.

Specific examples of the compound represented by the general formula (i), (ii), (iii) or (iv) are given below, but it should not be construed that the invention is limited thereto. In this respect, L may be combined with any of specific examples of L as described later and may be any other than those described herein.

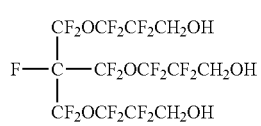
(i-1)

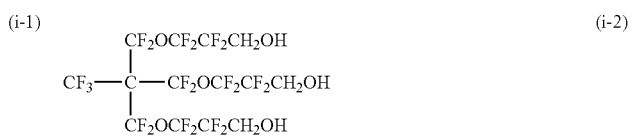
(i-2)

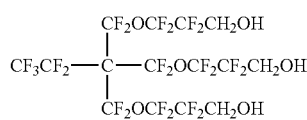
(i-3)

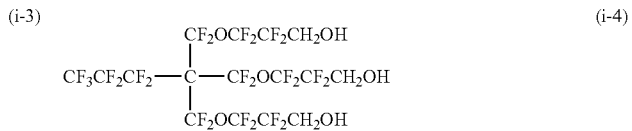
(i-4)

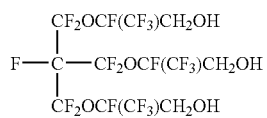
(i-5)

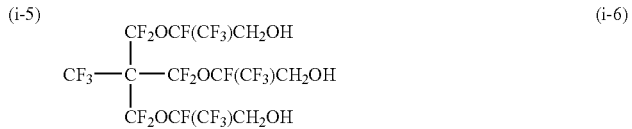
(i-6)

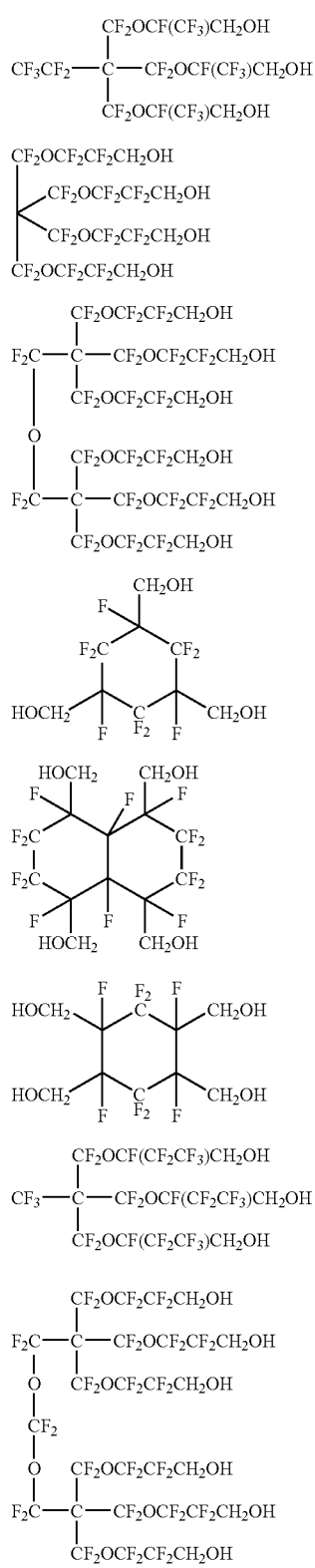

-continued
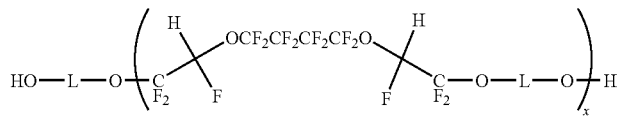
(i-25)
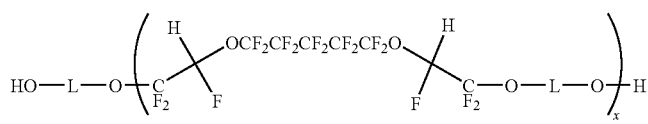
(i-26)
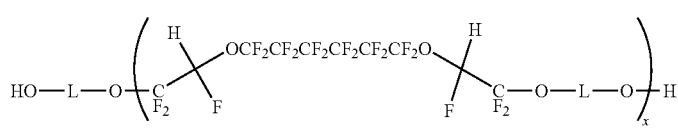
(i-27)
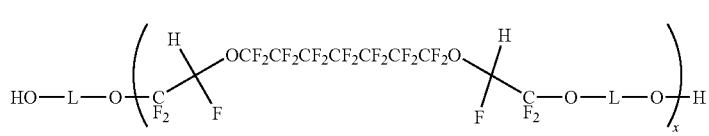
(i-28)
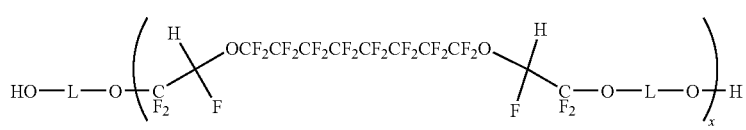
(i-29)
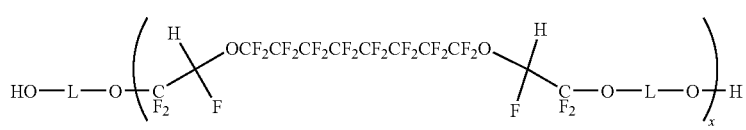
(i-30)
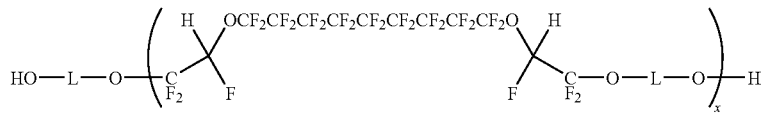
(i-31)
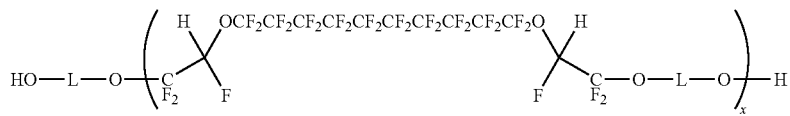
(i-32)
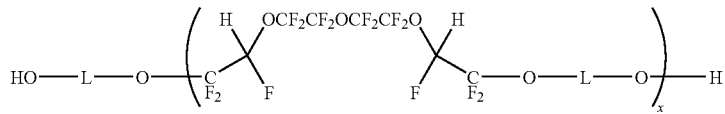
(i-33)
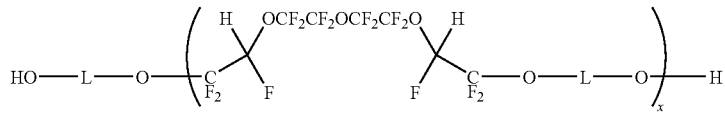
(i-34)
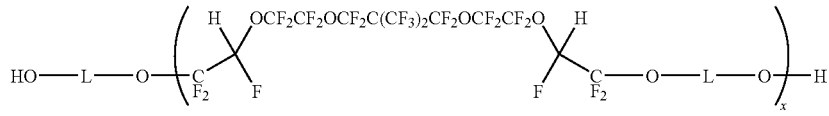
(i-35)
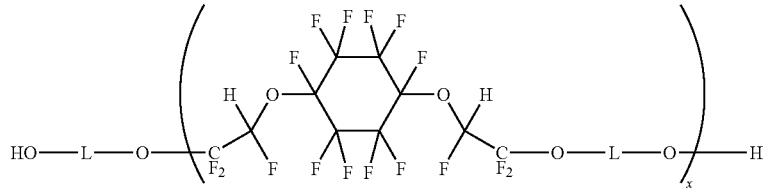

-continued
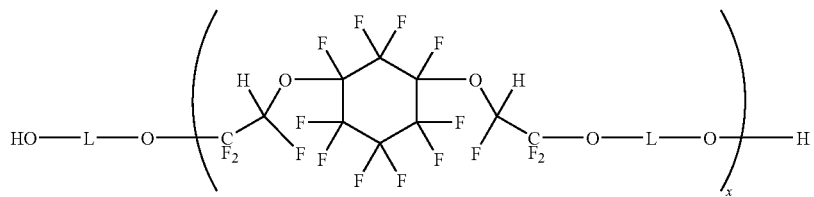
(i-36)
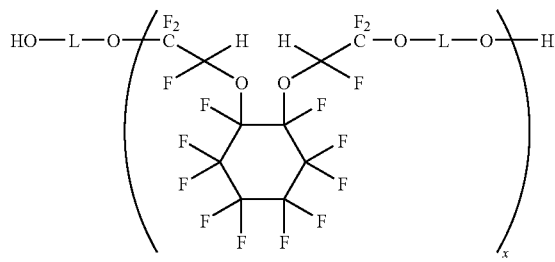
(i-37)
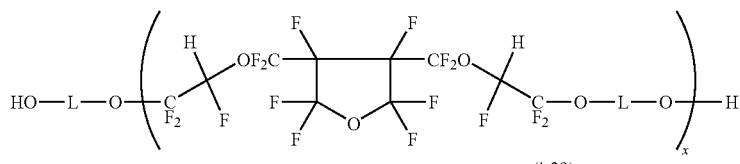
(i-38)
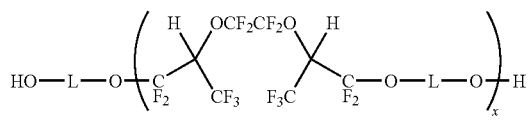
(i-39)
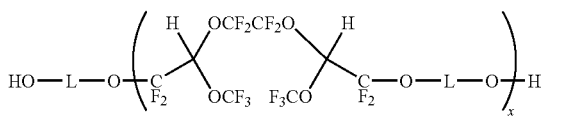
(i-40)
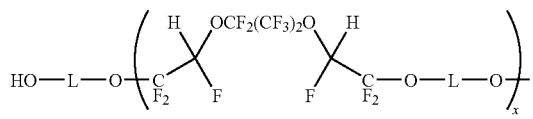
(i-41)
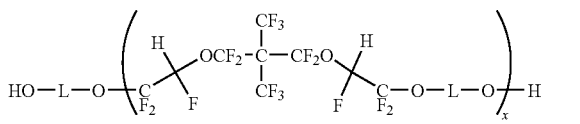
(i-42)
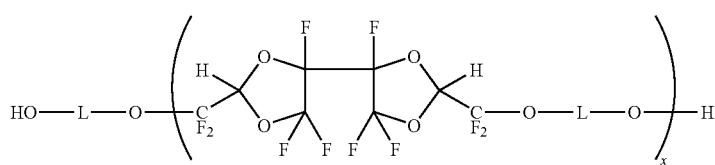
(i-43)
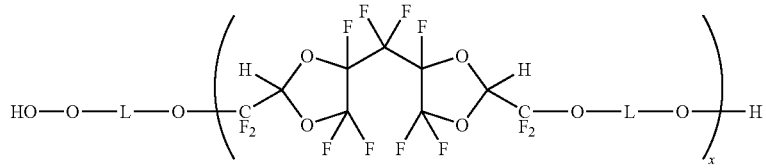
(i-44)
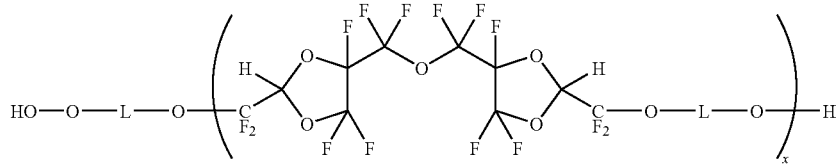
(i-45)
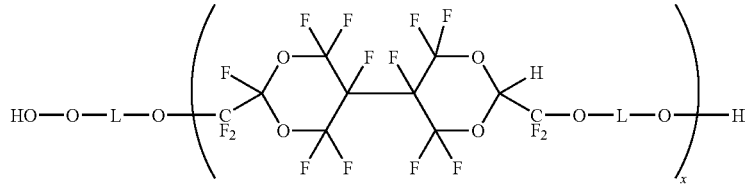
(i-46)

(i-47)

(i-48)

(i-49)

| | |
|---|---|
| HOCH$_2$(CF$_2$)$_4$CH$_2$OH (i-50) | HOCH$_2$(CF$_2$)$_6$CH$_2$OH (i-51) |
| HOCH$_2$(CF$_2$)$_8$CH$_2$OH (i-52) | HOCH$_2$(CF$_2$)$_{10}$CH$_2$OH (i-53) |
| HOCH$_2$(CF$_2$)$_{12}$CH$_2$OH (i-54) | HOCH$_2$CF$_2$(CF$_2$CF$_2$O)$_y$CF$_2$CH$_2$OH (i-55) |

HOCH$_2$CF$_2$(CF$_2$CF$_2$O)$_y$(CF$_2$O)$_z$CF$_2$CH$_2$OH (i-56)

In the foregoing (i-55) and (i-56), x represents an integer of from 1 to 200; and each of y and z represents an integer of from 1 to 200, and preferably an integer of from 3 to 100.

Specific examples of the divalent organic group L are given below, but it should not be construed that the invention is limited thereto.

—CH$_2$CF$_2$CH$_2$— (L-1)

—CH$_2$CF$_2$CF$_2$CH$_2$— (L-2)

—CH$_2$CF$_2$CF$_2$CF$_2$CH$_2$— (L-3)

—CH$_2$CF$_2$CF$_2$CF$_2$CF$_2$CH$_2$— (L-4)

—CH$_2$CF$_2$CF$_2$CF$_2$CF$_2$CF$_2$CH$_2$— (L-5)

—CH$_2$CF$_2$CF$_2$CF$_2$CF$_2$CF$_2$CF$_2$CH$_2$— (L-6)

—CH$_2$CF$_2$CF$_2$CF$_2$CF$_2$CF$_2$CF$_2$CF$_2$CH$_2$— (L-7)

—CH$_2$CF$_2$CF$_2$CF$_2$CF$_2$CF$_2$CF$_2$CF$_2$CF$_2$CH$_2$— (L-8)

—CH$_2$CF$_2$CF$_2$CF$_2$CF$_2$CF$_2$CF$_2$CF$_2$CF$_2$CF$_2$CF$_2$CH$_2$— (L-9)

—CH$_2$CF$_2$OCF$_2$CH$_2$— (L-10)

—CH$_2$CF$_2$CF$_2$OCF$_2$CF$_2$CH$_2$ (L-11)

—CH$_2$CF$_2$OCF$_2$C(CF$_3$)$_2$CF$_2$OCF$_2$CH$_2$— (L-12)

-continued (L-13) —CH$_2$C(CF$_3$)(F)OCF$_2$—C(CF$_3$)(CF$_3$)—CF$_2$O—C(CF$_3$)(F)CH$_2$—

(L-14) perfluorocyclohexane-1,4-diyl-bis(methylene)

(L-15) perfluorocyclohexane-1,3-diyl-bis(methylene)

(L-16) perfluorocyclohexane-1,2-diyl-bis(methylene)

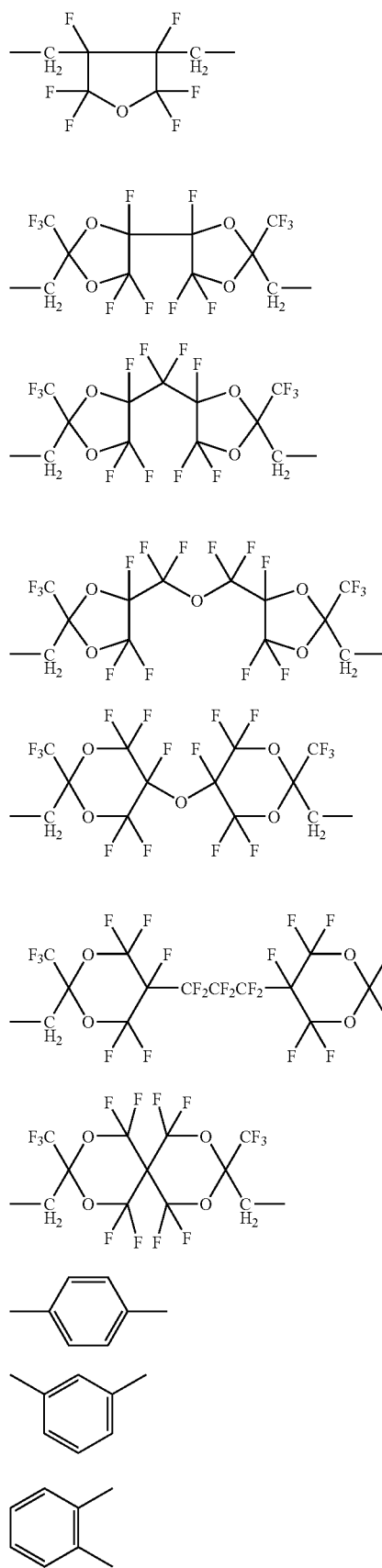
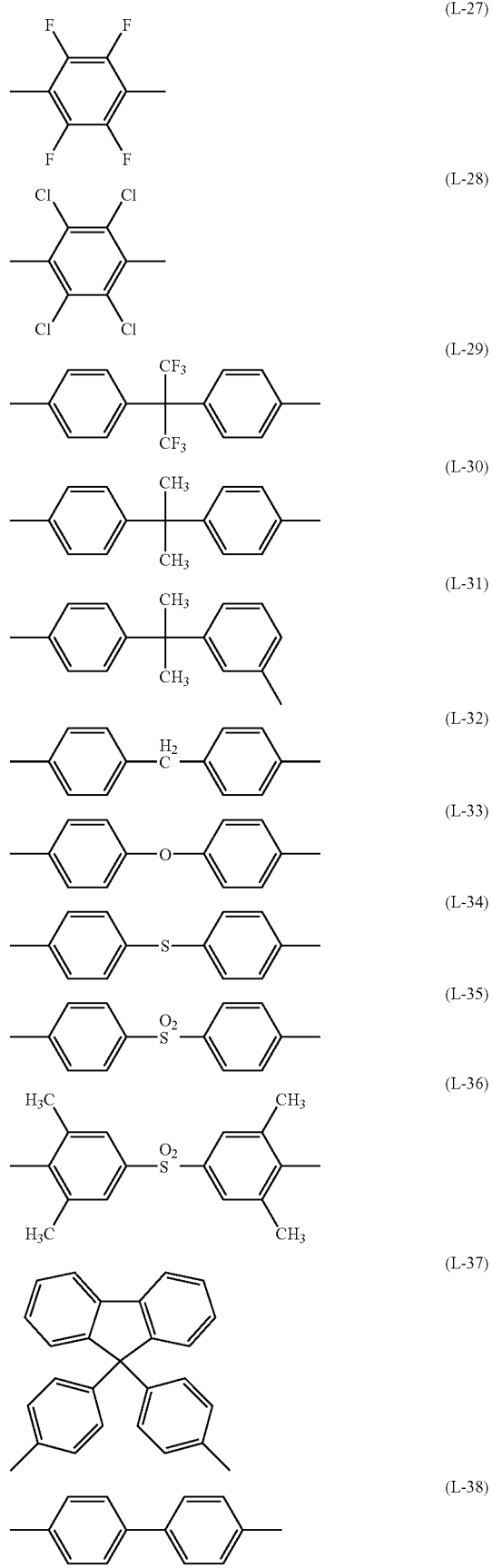

-continued

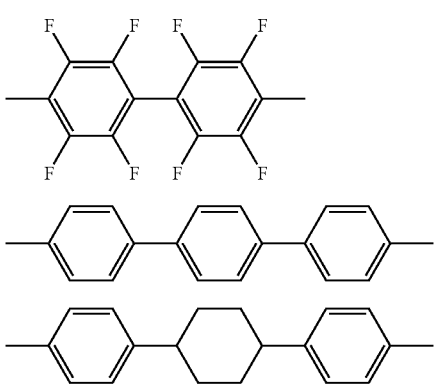

(L-39)

(L-40)

(L-41)

Specific examples of the isocyanate represented by the general formula (VII) are given below, but it should not be construed that the invention is limited thereto.

$(OCN(CH_2)_3Si(OCH_3)_3$ (VII-1)

$OCN(CH_2)_3Si(OC_2H_5)_3$ (VII-2)

$OCN(CH_2)_3Si(OC_2H_5)_2CH_3$ (VII-3)

$OCN(CH_2)_5Si(OCH_3)_3$ (VII-4)

$OCN(CH_2)_5Si(OCH_3)_3$ (VII-5)

$OCN(CH_2)_6Si(OCH_3)_3$ (VII-6)

$OCN(CH_2)_3Si(OC_2H_5)_2Ph$ (VII-7)

$OCN(CH_2)_3Si(OH)_3$ (VII-8)

$OCN(CH_2)_3Si(NCO)_3$ (VII-9)

$OCN(CH_2)_3Si(OCOCH_3)_3$ (VII-10)

Such an isocyanate can be produced by a known method. Also, some isocyanates are commercially available. For example, the compound (VII-2) is available from Sigma-Aldrich Japan K.K., Wako Pure Chemical Industries, Ltd. and so on.

Specific examples of the compound represented by the general formula (I) include adducts composed of an arbitrary combination of the specific examples of the general formula (i) and the specific examples of the general formula (VII) as described previously, but it should not be construed that the invention is limited thereto.

The compound represented by the general formula (II), general formula (iii) or general formula (Iv) can be synthesized through an addition reaction between a perfluorodiene represented by the following general formula (II'), general formula (III') or general formula (IV') and a diol represented by the following general formula (VIII) while using an excessive amount (preferably from 1.05 times to 2 times, and more preferably from 1.1 times to 1.5 times in terms of a molar ratio) of the diol represented by the general formula (VIII) relative to the perfluorodiene represented by the general formula (II'), general formula (III') or formula (IV'). The respective symbols in the following general formulae (II') and (III') are synonymous with the symbols in the foregoing general formulae (II) and (iii). Also, in the general formula (VIII), L represents a divalent organic group and is synonymous with L in the foregoing general formula (II).

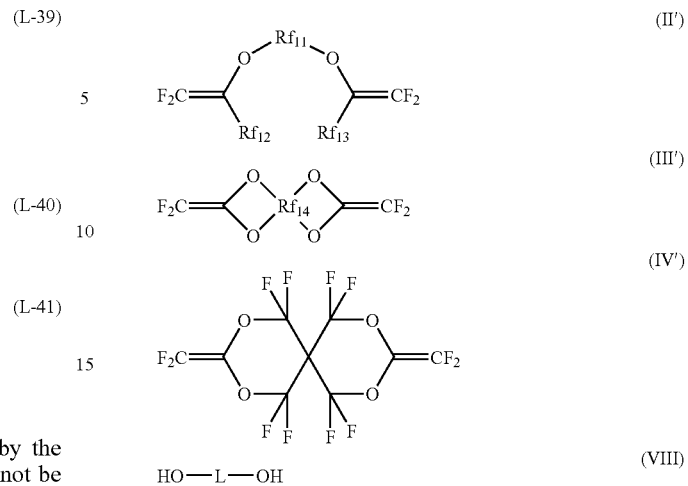

HO—L—OH (VIII)

The compound represented by the general formula (I) can be produced by a method disclosed in, for example, JP-A-2006-28280, JP-A-2008-106036, JP-A-2007-230992 and JP-A-2008-174464. Alternatively, some compounds or precursors thereof are commercially available and are available from, for example, Sigma-Aldrich Japan K.K., Ausimont S.p.A., Exfluor Research Corporation and so on.

The perfluorodiene compound can be produced by a method disclosed in, for example, JP-A-2001-240576, JP-A-2006-131613 and JP-A-2007-131615.

In the invention, though the fluorine-containing diene is used as a production intermediate of a part of the fluorine-containing polyfunctional silicon compound, since such a compound has a chemically different structure from the dienes and olefins in the foregoing Non-Patent Document 1 and Patent Document 2, it is different in a production method. Also, in view of the fact that dienes and olefins having various structures can be relatively easily produced by a know method (for example, methods disclosed in JP-A-2001-240576, JP-A-2006-131613 and JP-A-2007-131615), a problem in availability of the raw material could be solved.

The fluorine-containing polyfunctional silicon compound of the invention can be formed into a polymer material, a film material, a coating agent or the like upon being polycondensed. A mass average molecular weight (measured by GPC on the basis of polystyrene) of the polymer is preferably from 1,000 to 1,000,000, and a degree of dispersion thereof is preferably from 1.1 to 2.

A processed substrate having a film formed using a composition containing the fluorine-containing polyfunctional silicon compound of the invention on a substrate is excellent from the viewpoints of water repellency, scratch resistance, low refraction properties and the like. In the composition, a content of the fluorine-containing polyfunctional silicon compound is preferably from 5 to 98% by mass relative to the whole of solids. The composition can contain a solvent, a catalyst, a ligand compound and the like. As the solvent, though any solvent capable of dissolving or dispersing the fluorine-containing polyfunctional silicon compound of the invention therein can be used without particular limitations, water, methanol, ethanol, methyl ethyl ketone, trifluoroethanol and the like are preferable. Though the catalyst is not particularly limited so far it is a compound capable of hydrolyzing and polycondensing the fluorine-containing polyfunctional silicon compound of the invention, a mineral acid (for example, hydrochloric acid, sulfuric acid, etc.), a carboxylic acid (for example, acetic acid, benzoic acid, etc.), a sulfonic acid (for example, p-toluenesulfonic acid, etc.), an amine (for example, ammonia, ethylamine, pyridine, etc.), an alkali metal or alkaline earth metal hydroxide (for example, sodium hydroxide, potassium hydroxide, etc.), a Lewis acid compound (for example, ethyl orthotitanate, ammonium tris(ethyl acetoacetate), iron chloride, etc.) and the like are preferable. As the ligand compound, for example, acetylacetone, methyl acetoacetate and the like are preferable. Also, for the purpose of enhancing film surface properties, a surfactant may be used. The surfactant is not particularly limited, and conventionally known surfactants can be used; and examples thereof include a nonionic surfactant (for example, a polyoxyethylene alkyl ether, etc.), an anionic surfactant (for example, an alkanesulfonic acid salt, etc.), a cationic surfactant (for example, a quaternary ammonium salt, etc.), an ampholytic surfactant (for example, a carboxy betaine, etc.), a fluorine based surfactant (for example, a perfluoroalkane carboxylic acid salt, etc.) and the like. Of these, the fluorine based surfactant is preferably used because it has high compatibility with the fluorine-containing polyfunctional silicon compound of the invention. Examples of a method for forming a film include a method for coating the composition on the substrate and drying it and the like. A coating method is not particularly limited, and a method, for example, a spray coating method, a dip coating method, a flow coating method, a spin coating method, a roll coating method, a film applicator method, a screen printing method, a bar coater method, brush coating, sponge coating, etc. can be applied. Examples of a drying method include heat drying, and it is preferable to perform drying at from 50° C. to 200° C. for from 2 minutes to 60 minutes. A thickness of the film is preferably from 0.01 µm to 1,000 µm.

It is preferable that the surface of the film is excellent in water repellency, and it is preferable that a water droplet contact angle is from 85° to 180°. Also, it is preferable that the surface of the film is excellent in water droplet sliding properties, and it is preferable that a sliding angle is from 0.1° to 25°.

The invention is hereunder described in more detail with reference to the following Examples, but it should not be construed that the invention is limited thereto.

EXAMPLES

Example 1

In a methyl ethyl ketone (10 mL) solution of (i-9) (1.2 g, 1.5 mmoles), potassium carbonate (1.0 g, 7.25 mmoles) was added at room temperature, to which was then further added dropwise (VII-2) (1.5 g, 6.1 mmoles). The reaction solution was stirred at room temperature for 3 hours; thereafter, an insoluble matter was removed by celite filtration; and a filtrate was concentrated in vacuo to obtain a fluorine-containing polyfunctional silicon compound A (2.6 g). This compound A was subjected to NMR measurement and mass analysis. As a result, it was confirmed that a compound having the following structure was obtained.

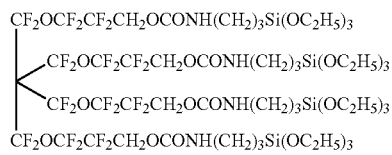

$^1$H NMR [CO(CD$_3$)$_2$] δ: 0.61 (t, J=8.25, 8H), 1.18 (t, J=7.05 Hz, 36H), 1.63 (m, 8H), 3.16 (m, 8H), 3.81 (t, J=7.05 Hz, 24H), 4.63 (t, J=13.8, 8H), 6.73 (bs, 4H)

$^{19}$F NMR [CO(CD$_3$)$_2$] δ: −66.34 (8F), −86.37 (8F), −124.23 (t, J=13.8, 8F)

MARDI-MS Found: m/z=1811.51; (M+Na), Calcd.: m/z=1811.50; (M+Na).

Example 2

In a methyl ethyl ketone (10 mL) solution of (i-9) (1.2 g, 1.5 mmoles), potassium carbonate (1.0 g, 7.25 mmoles) was added at room temperature, to which was then further added dropwise (VII-2) (1.1 g, 4.5 mmoles). The reaction solution was stirred at room temperature for 3 hours; thereafter, an insoluble matter was removed by celite filtration; and the filtrate was concentrated in vacuo to obtain a fluorine-containing polyfunctional silicon compound B (2.2 g). This compound B was subjected to NMR measurement. As a result, it was confirmed that the product was a mixture containing B-2, B-3 and the like in addition to a main product B-1. A molar ratio of these compounds calculated from a result of the NMR measurement was found to be B-1/B-2/B-3=55/20/25.

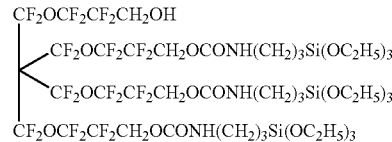

B-1

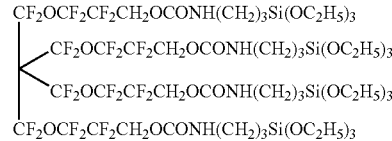

B-2

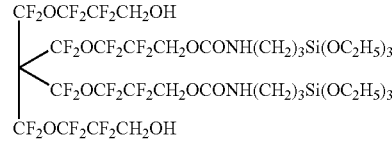

B-3

Example 3

In a methyl ethyl ketone (10 mL) solution of (i-53) (1.0 g, 1.78 mmoles), potassium carbonate (0.74 g, 5.36 mmoles) was added at room temperature, to which was then further added dropwise (VII-2) (0.88 g, 3.56 mmoles). The reaction solution was stirred at room temperature for 3 hours; thereafter, an insoluble matter was removed by celite filtration; and a filtrate was concentrated in vacuo to obtain a fluorine-containing polyfunctional silicon compound C (1.82 g). This compound C was subjected to NMR measurement. As a result, it was confirmed that a compound having the following structure was obtained.

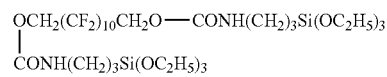

$^1$H NMR [CO(CD$_3$)$_2$] δ: 0.61 (m, 4H), 1.18 (t, J=6.90 Hz, 18H), 1.62 (m, 4H), 3.16 (m, 4H), 3.81 (q, J=6.90 Hz, 12H), 4.74 (t, J=13.8, 4H), 6.80 (bs, 2H)

$^{19}$F NMR [CO(CD$_3$)$_2$] δ: −120.4 (t, J=13.8, 4F), −122.3 (bs, 12F), −124.0 (bs, 4F)

MARDI-MS Found: m/z=1079.22; (M+Na), Calcd.: m/z=1079.24; (M+Na).

Example 4

A perfluorodiene 1 (1.0 g, 2.54 mmoles), a fluorine-containing diol 2 (1.64 g, 2.92 mmoles) and potassium carbonate (1.0 g, 7.25 mmoles) were stirred in methyl ethyl ketone (15 mL) at room temperature for 48 hours. A small amount of a supernatant was concentrated and subjected to NMR measurement. As a result, it was confirmed that the obtained compound had a structure of (i-25) [L=(L-9)] and that an average value of x was 7.8.

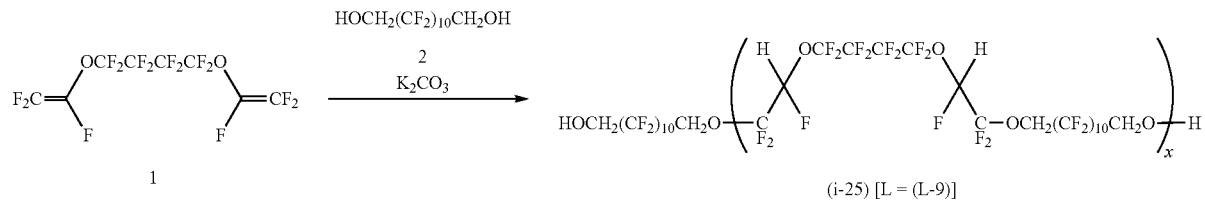

To the foregoing reaction solution, (VII-2) (0.099 g, 0.4 mmoles) was added, and the mixture was further stirred for 3 hours. An insoluble matter was removed by celite filtration; and a filtrate was concentrated in vacuo to obtain a fluorine-containing polyfunctional silicon compound D (2.60 g). This compound D was subjected to NMR measurement. As a result, it was confirmed that a compound having the following structure was obtained.

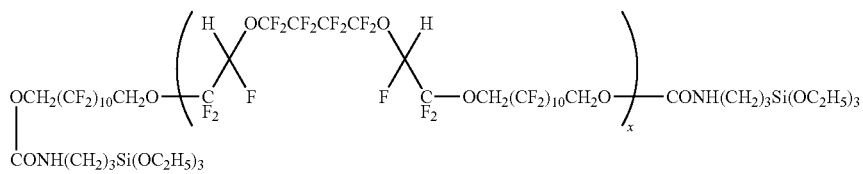

$^1$H NMR [CO(CD$_3$)$_2$] δ: 0.61 (m, 4H), 1.18 (t, J=7.05 Hz, 18H), 1.63 (m, 4H), 3.17 (m, 4H), 3.81 (q, J=7.05 Hz, 12H), 4.73 (t, J=13.8, 4H), 4.87 (t, J=12.8, 31.1H), 6.80 (bs, 2H), 6.85 (d, J=52.2, 15.6H)

Example 5

A perfluorodiene 3 (1.0 g, 2.50 mmoles), a fluorine-containing diol 2 (1.62 g, 2.87 mmoles) and potassium carbonate (1.0 g, 7.25 mmoles) were stirred in methyl ethyl ketone (15 mL) at room temperature for 48 hours. A small amount of a supernatant was concentrated and subjected to NMR measurement. As a result, it was confirmed that the obtained compound had a structure of (i-49) [L=(L-9)] and that an average value of x was 9.0.

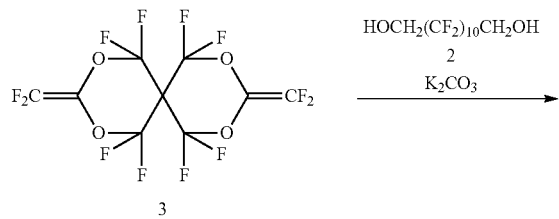

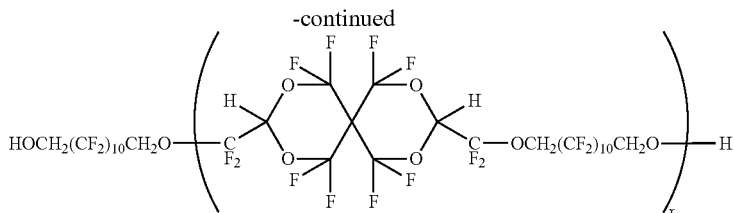

(i-49) [L = [L-9]]

To the foregoing reaction solution, (VII-2) (0.099 g, 0.4 mmoles) was added, and the mixture was further stirred for 3 hours. An insoluble matter was removed by celite filtration; and a filtrate was concentrated in vacuo to obtain a fluorine-containing polyfunctional silicon compound E (2.56 g). This compound E was subjected to NMR measurement. As a result, it was confirmed that a compound having the following structure was obtained.

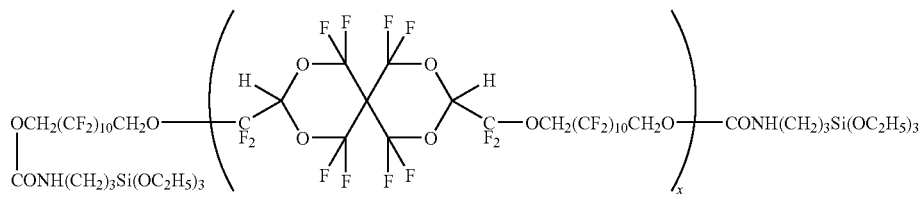

$^1$H NMR [CO(CD$_3$)$_2$] δ: 0.61 (m, 4H), 1.18 (t, J=7.05 Hz, 18H), 1.63 (m, 4H), 3.17 (m, 4H), 3.81 (q, J=7.05 Hz, 12H), 4.74 (t, J=14.1, 4H), 4.89 (t, J=12.8, 35.7H), 6.41 (bs, 17.7H), 6.77 (br, 2H)

Example 6

A perfluorodiene 3 (0.800 g, 2.0 mmoles), a fluorine-containing diol 4 (0.907 g, 2.2 mmoles) and potassium carbonate (0.69 g, 5.0 mmoles) were stirred in methyl ethyl ketone (10 mL) at room temperature for 50 hours. A small amount of a supernatant was concentrated and subjected to NMR measurement. As a result, it was confirmed that the obtained compound had a structure of (i-49) [L=(L-7)] and that an average value of x was 8.1.

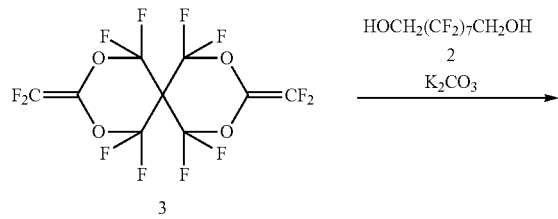

3

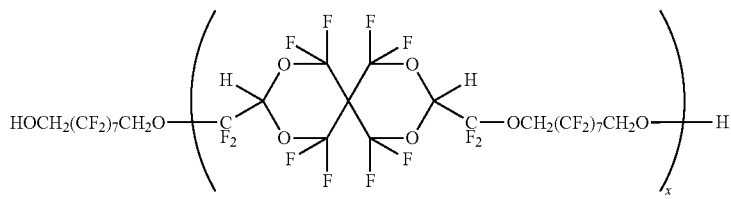

(i-49) [L = [L-7]]

To the foregoing reaction solution, (VII-2) (0.11 g, 0.45 mmoles) and potassium carbonate (0.1 g, 0.72 mmoles) were added, and the mixture was further stirred for 3 hours. An insoluble matter was removed by celite filtration; and a filtrate was concentrated in vacuo to obtain a fluorine-containing polyfunctional silicon compound F (1.70 g). This compound F was subjected to NMR measurement. As a result, it was confirmed that a compound having the following structure was obtained.

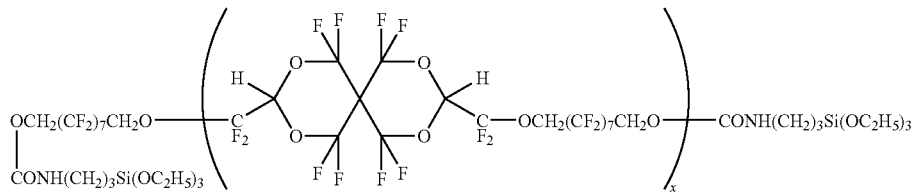

$^1$H NMR [CO(CD$_3$)$_2$] δ: 0.61 (m, 4H), 1.18 (t, J=7.05 Hz, 18H), 1.63 (m, 4H), 3.17 (m, 4H), 3.81 (q, J=7.05 Hz, 12H), 4.73 (t, J=14.3, 4H), 4.89 (t, J=13.1, 32.4H), 6.42 (bs, 16.3H), 6.78 (br, 2H)

Example 7

A perfluorodiene 3 (0.800 g, 2.0 mmoles), a fluorine-containing diol 5 (0.577 g, 2.2 mmoles) and potassium carbonate (0.69 g, 5.0 mmoles) were stirred in methyl ethyl ketone (10 mL) at room temperature for 50 hours. A small amount of a supernatant was concentrated and subjected to NMR measurement. As a result, it was confirmed that the obtained compound had a structure of (i-49) [L=(L-4)] and that an average value of x was 7.6.

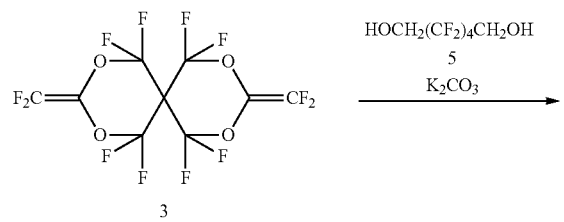

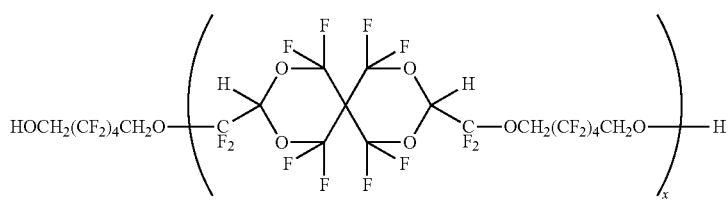

(i-49) [L = [L-4]]

To the foregoing reaction solution, (VII-2) (0.12 g, 0.49 mmoles) and potassium carbonate (0.1 g, 0.72 mmoles) were added, and the mixture was further stirred for 3 hours. An insoluble matter was removed by celite filtration; and a filtrate was concentrated in vacuo to obtain a fluorine-containing polyfunctional silicon compound G (1.38 g). This compound G was subjected to NMR measurement. As a result, it was confirmed that a compound having the following structure was obtained.

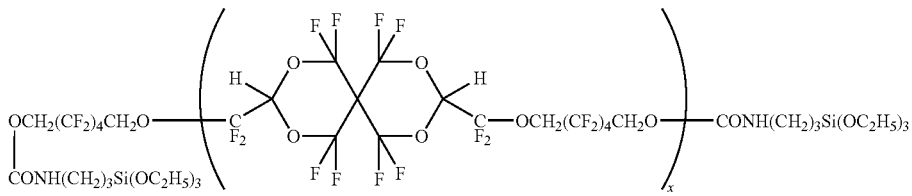

$^1$H NMR [CO(CD$_3$)$_2$] δ: 0.62 (m, 4H), 1.18 (t, J=7.05 Hz, 18H), 1.63 (m, 4H), 3.16 (m, 4H), 3.81 (q, J=7.05 Hz, 12H), 4.69 (t, J=14.4, 4H), 4.84 (t, J=13.2, 30.1H), 6.41 (bs, 15.2H), 6.75 (br, 2H)

Example 8

The reaction was carried out in the same manner as in Example 1, except for using 1.4 g (6.4 mmoles) of (VII-3) in place of the compound (VII-2), thereby obtaining the following compound H (1.8 g).

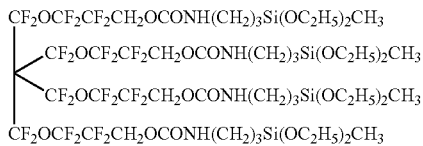

$^1$H NMR [CO(CD$_3$)$_2$] δ: 0.26 (s, 12H), 0.59 (t, J=8.25, 8H), 1.18 (t, J=7.1 Hz, 24H), 1.62 (m, 8H), 3.15 (m, 8H), 3.80 (t, J=7.1 Hz, 16H), 4.63 (t, J=13.8, 8H), 6.73 (bs, 4H)
$^{19}$F NMR [CO(CD$_3$)$_2$] δ: −66.34 (8F), −86.37 (8F), −124.23 (t, J=13.8, 8F)
MARDI-MS Found: m/z=1691.45; (M+Na), Calcd.: m/z=1691.46; (M+Na).

Example 9

Evaluation of Fluorine-Containing Polyfunctional Silicon Compounds A to G and Fluorine-Containing Compounds I and J CF$_3$(CF$_2$)$_3$CH$_2$CH$_2$Si(OC$_2$H$_5$)$_3$    I CF$_3$(CF$_2$)$_7$CH$_2$CH$_2$Si(OC$_2$H$_5$)$_3$    J (Preparation of Coating Solution)

An ethanol (30 mL) solution of ethyl orthotitanate (0.05 g) and acetylacetone (0.044 g) was stirred at room temperature for 10 minutes, water (0.01 mL) was then added, and the mixture was further stirred at room temperature for one hour, thereby preparing a catalyst solution.

To this solution, a methyl ethyl ketone (25 mL) solution of the fluorine-containing polyfunctional silicon compound A (0.5 g) and water (0.75 mL) were added, and the mixture was stirred at room temperature for 4 hours and then allowed to stand overnight, thereby preparing a solution A. Also, solutions B to G, I and J were prepared by the same method, except for using each of the compounds B to G, I and J in place of the compound A.

(Preparation of Processed Substrate)

150 μL, of the solution A was spin coated (rotation rate: 2,000 rpm, rotation time: 20 seconds) on a glass plate of 5 cm×5 cm and heated at 150° C. for 30 minutes, thereby preparing a processed substrate A. A film thickness formed on the substrate was about 0.1 μm. Also, processed substrates B to G, I and J were prepared by the same method, except for using each of the solutions B to G, I and J in place of the solution A.

(Evaluation of Water Repellency)

A water contact angle of each of the processed substrates A to G, I and J was measured using a fully automated contact angle meter (DM700), manufactured by Kyowa Interface Science Co., Ltd. The results are shown in Table 1.

(Evaluation of Water Droplet Sliding Properties)

50 μL, of water was dropped on each of the processed substrates A to G, I and J, and a sliding angle thereof was measured using a fully automated contact angle meter (DM700), manufactured by Kyowa Interface Science Co., Ltd. The results are shown in Table 1.

(Evaluation of Scratch Resistance)

Using a steel wool #0000, manufactured by Nippon Steel Wool Co., Ltd, the processed substrate was rubbed 10 reciprocations under a load of 200 g/cm$^2$, and the degree of scratching (A: no scratch, B: not more than 10 scratches, C: from 10 to 30 scratches, D: 30 scratches or more) was visually determined. The results are shown in Table 1.

TABLE 1

| Processed substrate | Water contact angle (°) | Sliding angle (°) | Scratch resistance | Remark |
|---|---|---|---|---|
| A | 91 | 15 | A | Invention |
| B | 89 | 13 | A | Invention |
| C | 90 | 17 | B | Invention |
| D | 94 | 13 | B | Invention |
| E | 98 | 12 | B | Invention |
| F | 96 | 13 | B | Invention |
| G | 95 | 13 | B | Invention |
| I | 102 | 29 | C | Comparison |
| J | 108 | 28 | D | Comparison |

From the foregoing results, it is noted that though the fluorine-containing polyfunctional silicon compound of the invention is inferior in the water repellency to the conventional fluorine-containing silicon compound, it can serve as a raw material of coating materials which are excellent in the water droplet sliding properties and scratch resistance.

INDUSTRIAL APPLICABILITY

The fluorine-containing polyfunctional silicon compound of the invention is useful as a raw material for materials having high water repellency and excellent scratch resistance and water droplet sliding properties and can be produced by a production method which is simple and easy and environmentally friendly.

While the invention has been described in detail and with reference to specific embodiments thereof, it will be apparent to one skilled in the art that various changes and modifications can be made therein without departing from the spirit and scope thereof.

This application is based on a Japanese patent application (Japanese Patent Application No. 2008-30698), filed Feb. 12, 2008, the entire contents of which are hereby incorporated by reference.

The invention claimed is:

1. A fluorine-containing polyfunctional silicon compound represented by the following general formula (I):

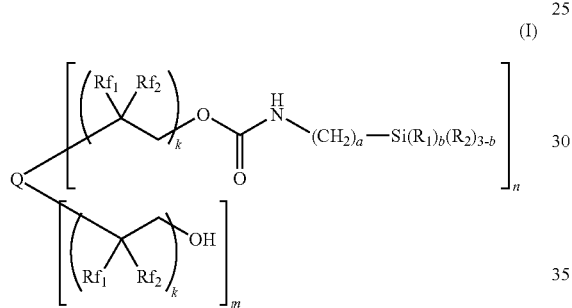

wherein in formula (I), Q represents an (n+m)-valent perfluoroalkyl group, which may have an ethereal oxygen atom; each of $Rf_1$ and $Rf_2$ independently represents a fluorine atom, a hydrogen atom or an alkyl group having at least one fluorine atom; $R_1$ represents a hydroxyl group, an isocyanate group or a hydrolyzable group; $R_2$ represents a hydrogen atom or a hydrocarbon group; k represents 0 or 1; n represents an integer of 2 or more; m represents an integer of 0 or more; a represents an integer of from 1 to 6; and b represents an integer of from 1 to 3, said compound being produced by reacting an (n+m)-valent fluorine-containing alcohol represented by the following general formula (I) and an isocyanate represented by the following general formula (VII) under a basic condition:

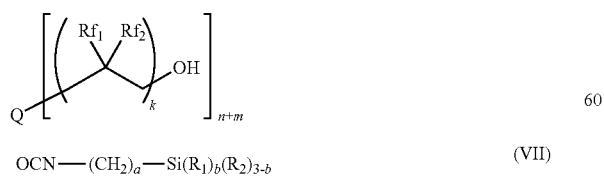

wherein in formulas (I) and (VII), Q represents an (n+m)-valent perfluoroalkyl group, which may have an ethereal oxygen atom; k represents 0 or 1; each of $Rf_1$ and $Rf_2$ independently represents a fluorine atom, a hydrogen atom or an alkyl group having at least one fluorine atom; $R_1$ represents a hydroxyl group, an isocyanate group or a hydrolyzable group; $R_2$ represents a hydrogen atom or a hydrocarbon group; n represents an integer of 2 or more; m represents an integer of 0 or more; a represents an integer of from 1 to 6; and b represents an integer of from 1 to 3, and wherein the (n+m)-valent fluorine-containing alcohol represented by the formula (i) is selected from the group consisting of the compounds (i-1) to (i-21) as follows:

(i-1)

(i-2)

(i-3)

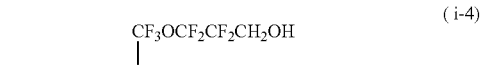
(i-4)

(i-5)

(i-6)

(i-7)

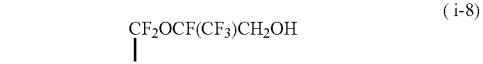
(i-8)

(i-9)

(i-10)

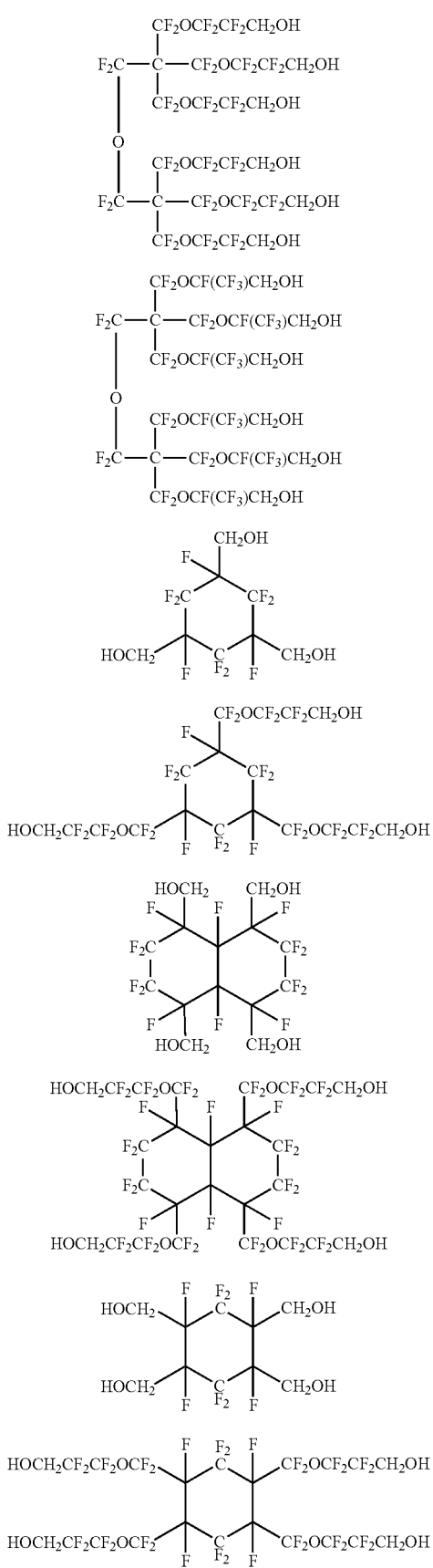

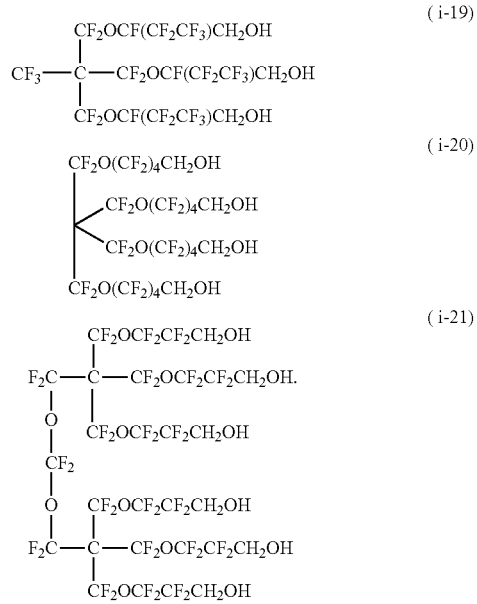

2. The fluorine-containing polyfunctional silicon compound according to claim 1, wherein, in the general formula (I), each of $Rf_1$ and $Rf_2$ independently represents a fluorine atom or a perfluoroalkyl group; and k represents 1.

3. A method for producing a fluorine-containing polyfunctional silicon compound represented by the following general formula (I), in which an (n+m)-valent fluorine-containing alcohol represented by the following general formula (I) and an isocyanate represented by the following general formula (VII) are reacted under a basic condition:

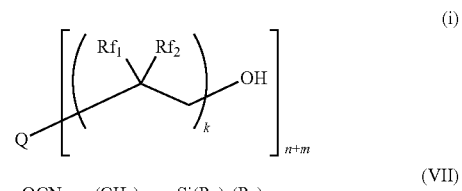

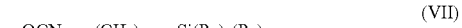

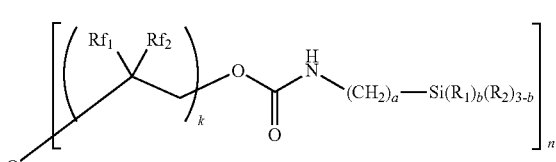

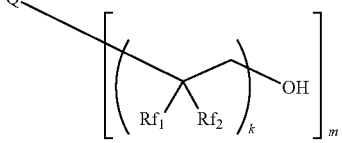

wherein Q represents an (n+m)-valent organic group having at least one fluorine atom; k represents 0 or 1; each of $Rf_1$ and $Rf_2$ independently represents a fluorine atom, a hydrogen atom or an alkyl group having at least one fluorine atom; $R_1$ represents a hydroxyl group, an isocyanate group or a hydrolyzable group; $R_2$ represents a hydrogen atom or a hydrocarbon group; n represents an integer of 2 or more; m represents an integer of 0 or more; a represents an integer of from 1 to 6; and b represents an integer of from 1 to 3,
and wherein the (n+m)-valent fluorine-containing alcohol represented by the formula (I) is selected from the group consisting of the compounds (1-1) to (1-21) as follows:
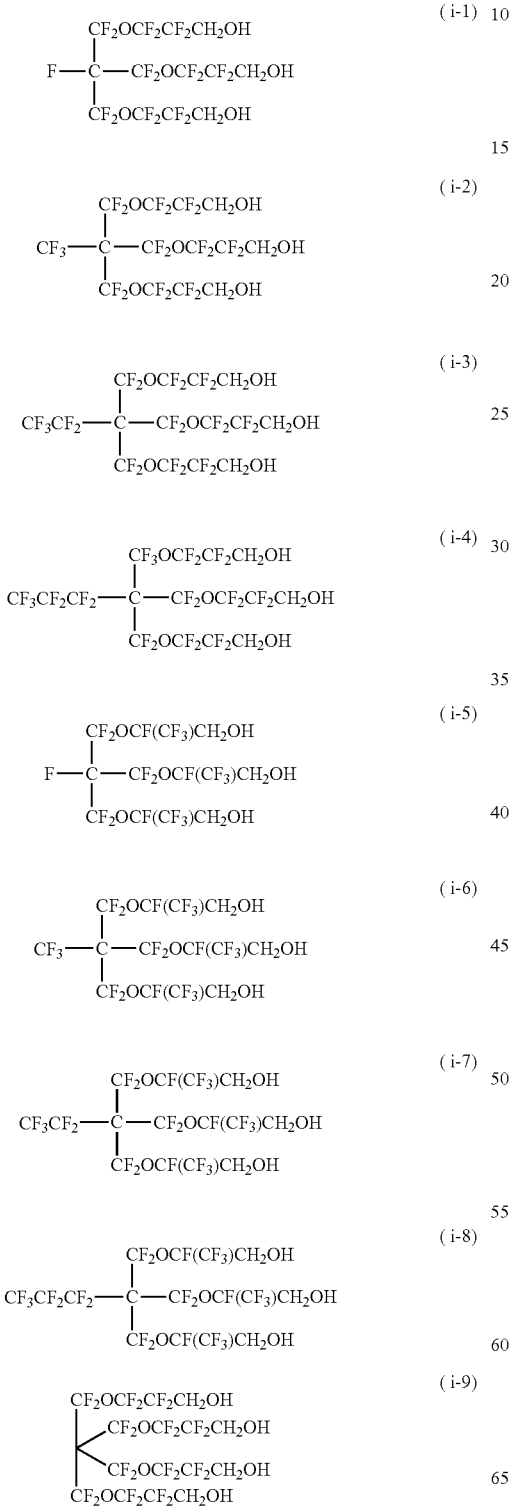
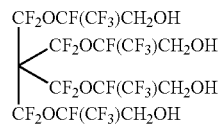
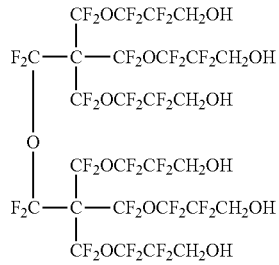
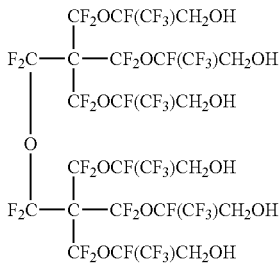
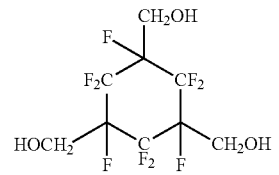
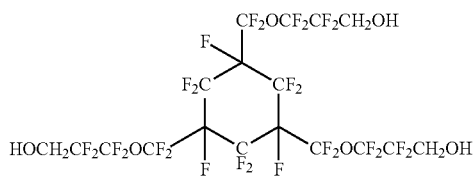
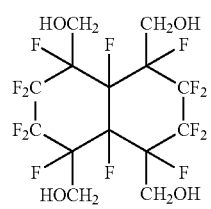
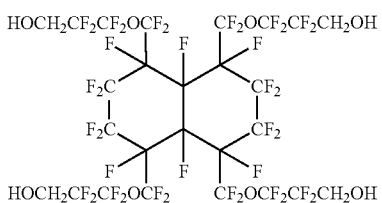
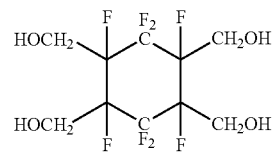

-continued

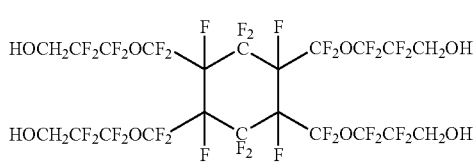
(i-18)

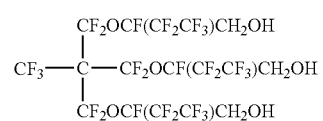
(i-19)

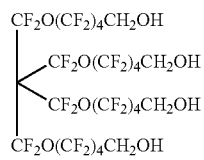
(i-20)

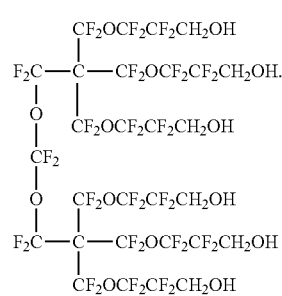
(i-21)

4. A method for producing of a fluorine-containing polyfunctional silicon compound represented by the following general formula (II), in which a fluorine-containing alcohol represented by the following general formula (II) and an isocyanate represented by the following general formula (VII) are reacted under a basic condition:

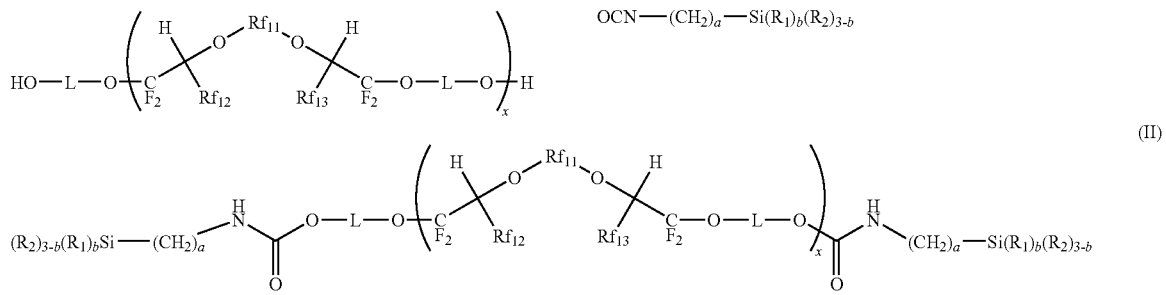

wherein $R_1$ represents a hydroxyl group, an isocyanate group or a hydrolyzable group; $R_2$ represents a hydrogen atom or a hydrocarbon group; a represents an integer of from 1 to 6; b represents an integer of from 1 to 3; x represents an integer of from 1 to 200; L represents a divalent organic group; $Rf_{11}$ represents a perfluoroalkylene group; each of $Rf_{12}$ and $Rf_{13}$ independently represents a fluorine atom, a perfluoroalkyl group or a perfluoroalkoxy group; and at least two of $Rf_{11}$, $Rf_{12}$ and $Rf_{13}$ may be bonded to each other to form one or more rings.

5. A method for producing of a fluorine-containing polyfunctional silicon compound represented by the following general formula (III), wherein a fluorine-containing alcohol represented by the following general formula (III) and an isocyanate represented by the following general formula (VII) are reacted under a basic condition:

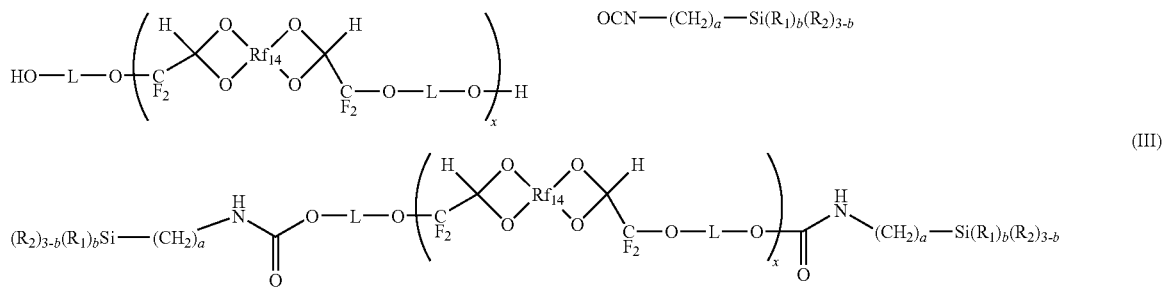

wherein $R_1$ represents a hydroxyl group, an isocyanate group or a hydrolyzable group; $R_2$ represents a hydrogen atom or a hydrocarbon group; a represents an integer of from 1 to 6; b represents an integer of from 1 to 3; x represents an integer of from 1 to 200; L represents a divalent organic group; and $Rf_{14}$ represents a tetravalent perfluoroalkylene group.

6. A method for producing of a fluorine-containing polyfunctional silicon compound represented by the following general formula (IV), wherein a fluorine-containing alcohol represented by the following general formula (Iv) and an isocyanate represented by the following general formula (VII) are reacted under a basic condition:

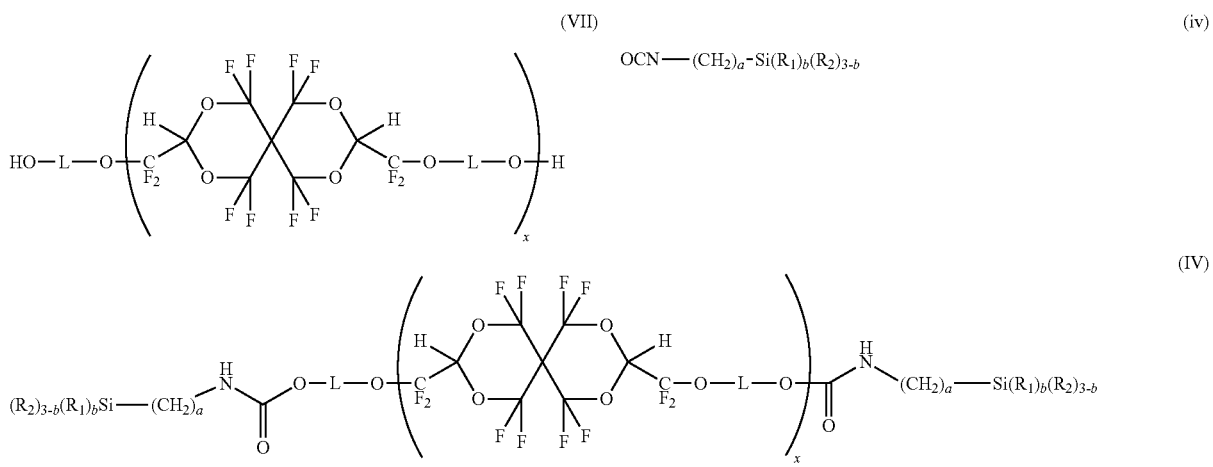

wherein $R_1$ represents a hydroxyl group, an isocyanate group or a hydrolyzable group; $R_2$ represents a hydrogen atom or a hydrocarbon group; a represents an integer of from 1 to 6; b represents an integer of from 1 to 3; x represents an integer of from 1 to 200; and L represents a divalent organic group.

7. The method for producing of a fluorine-containing polyfunctional silicon compound according to claim 4, wherein L is a divalent organic group represented by the following general formula (V) or (VI):

—$CH_2$—$Rf_{15}$—$CH_2$— (V)

—$Ar_1$— (VI)

wherein $Rf_{15}$ represents a divalent perfluoroalkyl group; and $Ar_1$ represents a divalent aryl group.

8. A processed substrate, which comprises a substrate having thereon a film formed from a composition containing the fluorine-containing polyfunctional silicon compound according to claim 1.

9. The method for producing of a fluorine-containing polyfunctional silicon compound according to claim 5, wherein L is a divalent organic group represented by the following general formula (V) or (VI):

—$CH_2$—$Rf_{15}$—$CH_2$— (V)

—$Ar_1$— (VI)

wherein $Rf_{15}$ represents a divalent perfluoroalkyl group; and $Ar_1$ represents a divalent aryl group.

10. The method for producing of a fluorine-containing polyfunctional silicon compound according to claim 6, wherein L is a divalent organic group represented by the following general formula (V) or (VI):

—$CH_2$—$Rf_{15}$—$CH_2$— (V)

—$Ar_1$— (VI)

wherein $Rf_{15}$ represents a divalent perfluoroalkyl group; and $Ar_1$ represents a divalent aryl group.

11. The fluorine-containing polyfunctional silicon compound according to claim 1, wherein, in the general formula (I), (n+m) represents an integer of 2 or more and not more than 6 and m represents an integer of not more than 5.

12. The fluorine-containing polyfunctional silicon compound according to claim 1, wherein m in formula (I) is 0.

13. The method for producing a fluorine-containing polyfunctional silicon compound according to claim 3, wherein m in formula (I) is 0.

14. A fluorine-containing polyfunctional silicon compound represented by the following general formula (I):

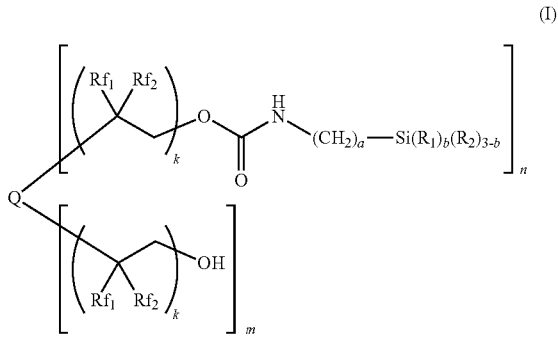

wherein Q represents an (n+m)-valent organic group having at least one fluorine atom; each of $Rf_1$ and $Rf_2$ independently represents a fluorine atom, a hydrogen atom or an alkyl group having at least one fluorine atom; $R_1$ represents a hydroxyl group, an isocyanate group or a hydrolyzable group; $R_2$ represents a hydrogen atom or a hydrocarbon group; k represents 0 or 1; n represents an integer of 2 or more; m represents an integer of 1 or more; a represents an integer of from 1 to 6; and b represents an integer of from 1 to 3.

* * * * *